(12) United States Patent
Dussaud et al.

(10) Patent No.: US 9,751,063 B2
(45) Date of Patent: Sep. 5, 2017

(54) EMULSION COMPOSITIONS AND APPLICATIONS THEREFOR

(71) Applicant: Momentive Performance Materials Inc., Waterford, NY (US)

(72) Inventors: Anne Dussaud, Tarrytown, NY (US); Sigfredo Gonzalez, Danbury, CT (US); Bhavna Rana, White Plains, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 46 days.

(21) Appl. No.: 14/564,645

(22) Filed: Dec. 9, 2014

(65) Prior Publication Data

US 2015/0157996 A1     Jun. 11, 2015

Related U.S. Application Data

(60) Provisional application No. 61/913,676, filed on Dec. 9, 2013.

(51) Int. Cl.

| | |
|---|---|
| *B01F 17/54* | (2006.01) |
| *B01F 17/00* | (2006.01) |
| *A61K 8/89* | (2006.01) |
| *C09G 1/04* | (2006.01) |
| *A61Q 17/04* | (2006.01) |
| *A61Q 5/00* | (2006.01) |
| *A61K 8/06* | (2006.01) |
| *A61Q 5/12* | (2006.01) |
| *A61Q 19/00* | (2006.01) |
| *A61K 8/81* | (2006.01) |
| *A61K 8/892* | (2006.01) |
| *A61K 8/893* | (2006.01) |
| *A61K 8/895* | (2006.01) |
| *A61K 8/898* | (2006.01) |

(52) U.S. Cl.
CPC .......... *B01F 17/0071* (2013.01); *A61K 8/062* (2013.01); *A61K 8/8152* (2013.01); *A61K 8/89* (2013.01); *A61K 8/892* (2013.01); *A61K 8/893* (2013.01); *A61K 8/895* (2013.01); *A61K 8/898* (2013.01); *A61Q 5/00* (2013.01); *A61Q 5/12* (2013.01); *A61Q 17/04* (2013.01); *A61Q 19/00* (2013.01); *B01F 17/005* (2013.01); *B01F 17/0021* (2013.01); *B01F 17/0028* (2013.01); *B01F 17/0057* (2013.01); *B01F 17/0085* (2013.01); *C09G 1/04* (2013.01); *A61K 2800/412* (2013.01); *A61K 2800/48* (2013.01); *A61K 2800/594* (2013.01)

(58) Field of Classification Search
CPC ........................................ C08G 77/26–77/388
USPC ...................................................... 528/10–43
See application file for complete search history.

(56) References Cited

U.S. PATENT DOCUMENTS

| | | |
|---|---|---|
| 8,241,615 B2 | 8/2012 | Shah |
| 8,557,227 B2 | 10/2013 | Simonnet et al. |
| 2006/0293213 A1 | 12/2006 | Uehara et al. |
| 2010/0112017 A1* | 5/2010 | Mizutani .............. A61K 8/0212 424/401 |
| 2010/0196292 A1 | 8/2010 | Carson et al. |
| 2011/0318295 A1* | 12/2011 | Shimizu .................. A61K 8/06 424/70.122 |
| 2012/0045403 A1 | 2/2012 | Ikebe et al. |
| 2012/0289649 A1 | 11/2012 | Wagner et al. |

FOREIGN PATENT DOCUMENTS

| | | |
|---|---|---|
| DE | 10 2007 039 007 | 2/2009 |
| FR | 2911501 | 7/2008 |
| JP | 2010235460 | 10/2010 |
| WO | 2011/129291 | 10/2011 |
| WO | 2012/056959 | 5/2012 |

OTHER PUBLICATIONS

Saxena et al. (WO2009094221 A1).*
Written Opinion and International Search Report PCT/US2014/069287 dated Mar. 10, 2015.

* cited by examiner

*Primary Examiner* — Robert A Wax
*Assistant Examiner* — Quanglong Truong
(74) *Attorney, Agent, or Firm* — Joseph S. Ostroff

(57) ABSTRACT

The present invention relates to oil-in-water emulsion-forming compositions having reduced whitening effect when applied on wet substrates. The oil-in-water emulsion compositions are suitable for use in personal care products, textile treatments, polishing products, gloss enhancements and water resistance treatments.

20 Claims, No Drawings

EMULSION COMPOSITIONS AND APPLICATIONS THEREFOR

BACKGROUND OF THE INVENTION

1. Field of the Invention

The present invention relates to oil-in-water emulsion-forming compositions, oil-in-water emulsions formed upon addition of water thereto, such emulsions having reduced whitening effect when applied to water-wet substrates. More particularly, this invention is related to the preparation of oil-in-water emulsion compositions with polysiloxane possessing at least one hydrophilic moiety that are suitable for use in personal care products, textile treatments, polishing products, gloss enhancements and water resistance treatments.

2. Description of Related Art

Conventional oil-in-water emulsions are well known. They are widely used in many applications, for example, in personal care products, such as skin care products and hair care products, textile treatments, polishing products, gloss enhancements and water resistance treatments for hard and soft substrates, such as stones, tiles, rubber, metallic surfaces, wood, textiles, leather, plastic surfaces etc.

Oil-in-water emulsions which contain high levels of oil are usually whitening when applied to water-wet substrates. A non-whitening (i.e., clear and transparent) appearance is an important product feature that is desired in applications such as sunscreen and moisturizer.

Accordingly, it is an object of the present invention to provide oil-in-water emulsion compositions having reduced whitening effect when applied to water-wet substrates that are suitable for use in personal care products, textile treatments, polishing products, gloss enhancements and water resistance treatments.

SUMMARY OF THE INVENTION

In accordance with one aspect of the invention, there is provided an oil-in-water emulsion-forming composition comprising:

(i) polysiloxane possessing at least one hydrophilic moiety;
(ii) polymeric aqueous thickener; and,
(iii) oil, the oil-in-water emulsion-forming composition forming a oil-in-water emulsion upon addition of water thereto, the average particle size of oil (iii) in the emulsion being at least 5 microns, the emulsion when applied to a water-wet substrate exhibiting no significant whitening effect.

The present invention provides oil-in-water emulsion compositions having reduced whitening effect when applied to water-wet substrates that are suitable for use in personal care products, textile treatments, polishing products, gloss enhancements and water resistance treatments.

DETAILED DESCRIPTION OF PREFERRED EMBODIMENTS

In the specification and claims herein, the following terms and expressions are to be understood as indicated herein below.

It will also be understood that any numerical range recited herein is intended to include all sub-ranges within that range and any combination of end points of said ranges or sub-ranges.

As used herein, the term "monovalent" in reference to a group means that the group is capable of forming one covalent bond per group. As used herein, the term "polyvalent" in reference to a group means that the group is capable of forming two or more covalent bonds per group.

As used herein, the term "hydrocarbon group" is a group consisting of carbon and hydrogen atoms and includes acyclic hydrocarbon groups, alicyclic hydrocarbon groups and aromatic hydrocarbon groups.

As used herein, the term "acyclic hydrocarbon group" means any straight chain or branched hydrocarbon group, preferably containing from 1 to 60 carbon atoms, which may be saturated or unsaturated. Suitable monovalent acyclic hydrocarbon groups include alkyl, alkenyl and alkynyl groups. Representative and non-limiting examples of monovalent acyclic hydrocarbon groups are methyl, ethyl, sec-butyl, tert-butyl, octyl, decyl, dodecyl, cetyl, stearyl, ethenyl, propenyl, and butynyl. Suitable divalent acyclic hydrocarbon groups include linear or branched alkylene groups. Representative and non-limiting examples of divalent acyclic hydrocarbon groups are methylene, ethylene, propylene, hexylene, methylethylene, 2-methylpropylene and 2,2-dimethylpropylene. Suitable trivalent acyclic hydrocarbon radicals include alkanetriyl radicals, such as, for example, 1,1,2-ethanetriyl, 1,2,4-butanetriyl, 1,2,8-octanetriyl and 1,2,4-hexanetriyl.

As used herein the term "alkyl" means any saturated straight or branched monovalent hydrocarbon group. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl and dodecyl.

As used herein the term "alkenyl" means any straight or branched monovalent hydrocarbon group containing at least one carbon-carbon double bond and preferably containing from 2 to 10 carbon atoms, such as, for example, ethenyl, 2-propenyl, 3-butenyl, 5-hexenyl and 7-octenyl.

As used herein, the term "alicyclic hydrocarbon group" means a group containing one or more hydrocarbon rings, preferably containing from 3 to 12 carbon atoms, which may optionally be substituted on one or more of the rings with one or more monovalent or divalent acyclic group containing preferably 1 to 6 carbon atoms. In the case of an alicyclic hydrocarbon group containing two or more rings, the rings may be fused rings in which the two rings share two or more carbon atoms in common, or rings that are bonded to each other through a covalent bond or divalent acyclic group. Suitable monovalent alicyclic hydrocarbon groups include, for example, cycloalkyl groups, such as cyclohexyl and cyclooctyl or cycloalkenyl groups, such as cyclohexenyl. Suitable divalent hydrocarbon groups include, saturated or unsaturated divalent monocyclic hydrocarbon radicals, such as, for example, 1,4-cyclohexylene. Suitable trivalent alicyclic hydrocarbon radicals include cycloalkanetriyl radicals such as, for example, 1-ethylene-2,4-cyclohexylene and 1-methylethylene-3-methyl-3,4-cyclohexylene.

As used herein, the term "aromatic hydrocarbon group" means a hydrocarbon group containing one or more aromatic rings, which may, optionally, be substituted on the aromatic rings with one or more monovalent or divalent acyclic groups preferably containing 1 to 6 carbon atoms. In the case of an aromatic hydrocarbon group containing two or more rings, the rings may be fused rings in which the rings share two or more carbon atoms in common, or rings that are bonded to each other through a covalent bond or divalent acyclic group. Suitable monovalent aromatic hydrocarbon include, for example, phenyl, tolyl, 2,4,6-trimethylphenyl, naphthyl and anthryl, as well as aralkyl groups, such as, for example, 2-phenylethyl. Suitable divalent aromatic hydrocarbon groups include divalent monocyclic arene groups such as, for example, 1,2-phenylene, 1,4-phenylene, 4-methyl-1,2-phenylene and phenylmethylene. Suitable trivalent aromatic hydrocarbon groups include, for example, 1,3,5-phenylene and 1,2,4-phenylene.

As used herein, the "whitening effect" is measured and calculated by the following formula:

$$\text{Whitening} = (\text{Intensity}_{picture(I)} - \text{Intensity}_{Picture(II)}) *100 / \text{Intensity}_{picture(I)}$$

The test for measuring the whitening effect, advantageously employing digital image analysis processing, (for example, the image analysis software "Image-Pro Plus Software" available from Media Cybernetics Inc., Rockville, Md.), the particular details of which are described below, measures the intensity of a control sample, Picture (I), and the intensity of a treated sample, Picture (II). The intensity of the digital image is obtained by calculating the mean grey pixel value. For example, $\text{Intensity}_{Picture\ (I)}$ is obtained by calculating the mean grey pixel value of the blank wet substrate image, and $\text{Intensity}_{Picture\ (II)}$ is obtained by calculating the mean grey pixel value of the treated substrate image. The whitening is considered significant when it is higher than 20%. The term "no significant whitening effect" means a whitening result of less than 20%.

As used herein, the term "yield point" means the stress at which an elastic material under increasing stress ceases to behave elastically.

Polysiloxane (i)

In one embodiment of the invention, the hydrophilic moiety of polysiloxane (i) is selected from the group consisting of polyether group, sugar group, polyhydroxylated hydrocarbon group and ionic group.

In one embodiment of the invention, polysiloxane (i) in the emulsion has the general formula (I)

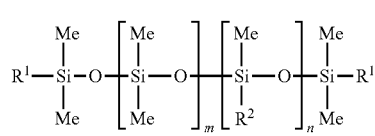
(I)

wherein $R^1$ is independently selected from the group consisting of monovalent hydrocarbon group having from 1 to 20 carbon atoms, optionally containing one or more heteroatoms and/or hydroxyl group, and alkoxy group $OR^3$ wherein $R^3$ is selected from the group consisting of monovalent hydrocarbon group having from 1 to 20 carbon atoms, optionally containing one or more heteroatoms and/or hydroxyl group, $R^2$ is a polyether group, m is from 0 to 50, preferable from 5 to 40, and more preferable from 10 to 20, n is from 1 to 50, preferable from 5 to 40, and more preferable from 10 to 20 and m+n is from 1 to 50, preferable from 5 to 40, and more preferable from 10 to 30.

In one embodiment of the invention, polysiloxane (i) in the emulsion has the general formula (II)

(II)

wherein
$M = R^4R^5R^6SiO_{1/2}$,
$D = R^7R^8SiO_{2/2}$,
$T = R^9SiO_{3/2}$,
$Q = SiO_{4/2}$,
with
a=1-10
b=0-1000
c=0-1
d=0-1
e=1-10
wherein
$R^4$, $R^5$, $R^6$, $R^7$, $R^8$ and $R^9$ are each independently an organic group, which comprises at least one group $R^{10}$, which is selected from:
$R^{11}$=—Z-(A-E)$_y$, wherein
Z=a bivalent or trivalent straight-chained, cyclic or branched, saturated or unsaturated $C_2$ to $C_{20}$-hydrocarbon group, which can comprise one or more groups selected from —O—, —NH—,

and can be substituted by one or more OH groups,
A is a bivalent group which is selected from the group which comprises:

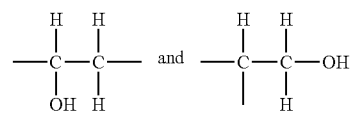

y=1 or 2
E is selected from the group which comprises:
$E^2$=—O—C(O)—$R^{12}$,
wherein $R^{12}$ is a straight-chained, cyclic or branched, saturated or unsaturated hydrocarbon group with up to 50 carbon atoms, which can comprise one or more groups selected from —O—, —NH—, —$NR^{13}$—, —C(O)— and is substituted by one or more OH groups,
wherein $R^{13}$ is a straight-chained, cyclic or branched, saturated or unsaturated hydrocarbon group with up to 6 carbon atoms, and
$E^3$=

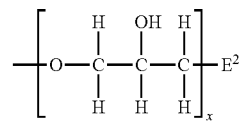

wherein $E^2$ is as defined above, and x=1-4,
$E^4$=—$NR^{14}R^{15}$, wherein
$R^{14}$ and $R^{15}$ are the same or different and are selected from the group which comprises:
hydrogen and straight-chained, cyclic or branched, saturated or unsaturated hydrocarbon group with up to 30 carbon atoms, which can comprise one or more groups selected from —O—, —NH—, —$NR^{13}$—, wherein $R^{13}$ is as defined above, —C(O)—, and can be substituted by one or more OH— and/or $H_2N$— groups, $R^{16}$=—Z-$E^2$ wherein $E^2$ is as defined above, and
$R^{17}$=—Z-$E^5$, wherein $E^5$=—NH—C(O)—$R^{14}$, wherein $R^{14}$ is a defined above, $R^{10}$ in addition to at least one of $R^{11}$, $R^{16}$ and $R^{17}$ may be $R^{18}$=—Z-$E^1$, wherein $E^1$ is —O—C(O)—$R^{19}$, wherein $R^{19}$ is a straight-chained, cyclic or branched, saturated or unsaturated hydrocarbon group with up to 50 carbon atoms, which can comprise one or more groups selected from —O—, —NH—, —$NR^{13}$—, —C(O)—, wherein $R^{13}$ is as defined above, but has no hydroxyl substituent.

In a preferred embodiment polysiloxane (i) according to the invention comprise structural elements selected from the following formulas:

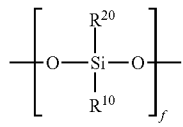

wherein $R^{10}$=$R^{11}$, $R^{16}$ and/or $R^{17}$, and optionally $R^{18}$, and, $R^{20}$=$C_1$ to $C_{22}$-alkyl, fluoroalkyl or aryl
f=0-600,

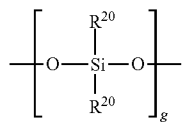

wherein the groups $R^{20}$ can be the same or different and are selected from $C_1$ to $C_{22}$-alkyl, fluoro-substituted $C_1$ to $C_{22}$-alkyl and aryl, and
g=0-700,

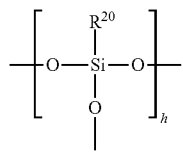

wherein $R^{20}$ is as defined above, and
h=0-10,

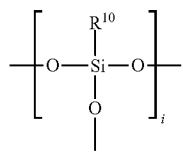

wherein $R^{10}$ is as defined above, and
i=0-10,

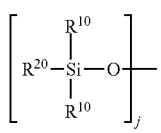

wherein $R^{10}$ and $R^{20}$ are as defined above, and
j=0-30,

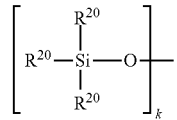

wherein $R^{20}$ is as defined above, and
k=0-30,

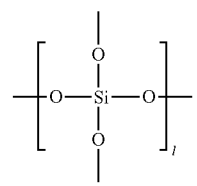

wherein l=0-10,
f+g+h+i+j+k+l=12 to 1000.

In a particularly preferred embodiment polysiloxane (i) according to the invention comprise two or more different groups $R^{10}$=$R^{11}$, $R^{16}$ and/or $R^{17}$ and optionally $R^{18}$. Preferably, the groups $R^{10}$ are selected from the groups $R^{11}$ and $R^{16}$.

In a further preferred embodiment of polysiloxane (i) according to the invention, the groups $R^{10}$=$R^{11}$, $R^{16}$ and/or $R^{17}$, preferably the groups $R^{11}$ and/or $R^{16}$, comprise one or more, preferably one (1), ester units (—C(O)O—).

In further preferred embodiments $R^{10}$ is selected according to the following clauses:
  $R^{10}$ is $R^{11}$ and/or $R^{16}$ and optionally $R^{18}$, or
  $R^{10}$ is $R^{17}$, and optionally $R^{18}$, or
  $R^{10}$ is $R^{11}$ and/or $R^{16}$ and $R^{17}$, and optionally $R^{18}$, the latter embodiment according to which $R^{10}$ comprises a hydroxy carboxylic acid group $R^{11}$ and/or $R^{16}$ and an amino-functional group $R^{17}$ being particularly preferred.

In a further preferred embodiment polysiloxane (i) according to the invention comprise two or more different groups $R^{10}$, which differ in their hydrophilic/lipophilic characteristics, corresponding to hydrophilic groups $R^{21}$ and lipophilic groups $R^{22}$:
  hydrophilic groups $R^{21}$ have a log P (25° C.) of <0.5, and
  lipophilic groups $R^{22}$ have a log P (25° C.) of ≥0.5,
wherein log P (25° C.) corresponds to the distribution coefficient of corresponding compounds H—$R^{21}$ and H—$R^{22}$, corresponding to compounds H—$R^{11}$, H—$R^{16}$ (and H—$R^{18}$ according to the optionally present group $R^{18}$) and H—$R^{17}$ in a water-n-octanol mixture at 25° C. According to the invention the corresponding distribution coefficients are determined, for the sake of simplicity, by means of the commercially available log P calculating software by the company ACD (ACD Inc., 133 Richmond St. W., Suite 605, Toronto, ON, Canada M5H 2L3 e.g. in Perspectives in Drug Discovery and Design, 19: 99-116, 2000) which are based on well-characterized log P contributions of single atoms structure fragments and intramolecular interaction between different fragments. Alternatively, the experimental determination in a water/n-octanol mixture (water: 50 ml, octanol: 50 ml, substance to be determined H—$R^{21}$ and H—$R^{22}$: 1 ml) at 25° C. is also possible.

In a further preferred embodiment polysiloxane (i) according to the invention comprise structural elements selected from the following formulas:

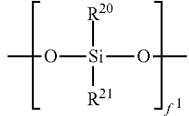

wherein $R^{20}=C_1$ to $C_{22}$-alkyl, fluoroalkyl or aryl, preferably methyl, $R^{21}$ is as defined above or below, and $f^1=1-300$, preferably 2 to 200, more preferably 2 to 50, even 3 to 30,

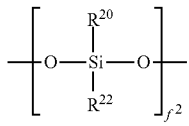

wherein $R^{20}=C_1$ to $C_{22}$-alkyl, fluoroalkyl or aryl, preferably methyl, and $R^{22}$ is as defined above or below, and $f^2=1-300$, preferably 2 to 200, more preferably 2 to 50, even 4 to 40,

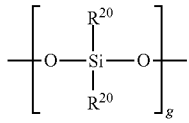

wherein the groups $R^{20}$ can be the same or different and are selected from $C_1$ to $C_{22}$-alkyl, fluoro-substituted $C_1$ to $C_{22}$-alkyl and aryl, preferably methyl, and $g=0-700$, preferably 3 to 500, more preferably 5 to 200, even more preferably 10 to 100,

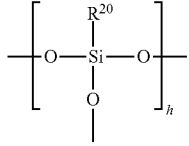

wherein $R^{20}$ is, as defined above, preferably methyl, and $h=0-10$, preferably 0,

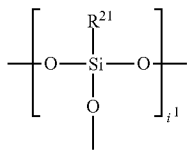

wherein $R^{21}$ is as defined above or below, and $i^1=0-5$, preferably 0,

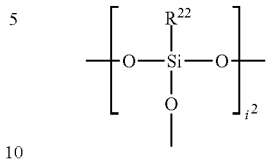

wherein $R^{22}$ is as defined above or below, and $i^2=0-5$, preferably 0,

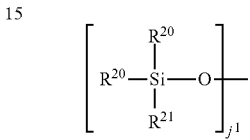

wherein $R^{20}$ is, as defined above, preferably methyl, and $R^{22}$ is as defined above or below, and $j^1=0-15$, preferably 0,

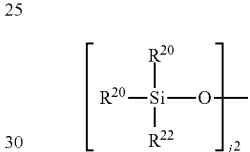

wherein $R^{20}$ is, as defined above, preferably methyl, and $R^{22}$ is as defined above or below, and $j^2=0-15$, preferably 0,

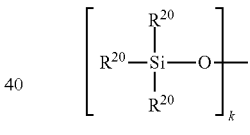

wherein $R^{20}$ is, as defined above, preferably methyl, and $k=0-30$, preferably 1 to 6, more preferably 2,

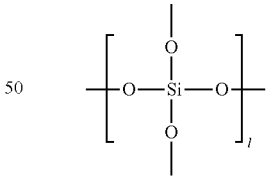

wherein $l=0-10$, preferably 0, $f^1+f^2+g+h+i^1+i^2+j^1+j^2+k+l=12$ to 1000, preferably 15 to 400, more preferably 20 to 200, even more preferably 30 to 150.

Preferably the molar ratio of the hydrophilic groups $R^{21}$ and the lipophilic groups $R^{22}$ in the polysiloxane compounds according to the invention amounts to from 5:1 to 1:10, more preferably from 2:1 to 1:7, even more preferably from 1:1 to 1:5.

In a preferred embodiment the group $R^{21}$ and the lipophilic groups $R^{22}$ in the polysiloxane compounds according to the invention amounts to from 5:1 to 1:100, more preferably from 5:1 to 1:50.

Preferably the molar ratio of the $R^{21}$ as well as $R^{22}$-comprising siloxy units to the "non-modified", only $R^{20}$-comprising siloxy units is 5:1 to 1:10, more preferably 2:1 to 1:7, even more preferably from 1:1 to 1:5. The polysiloxane compounds in which the ratio $R^{21}$ to $R^{22}$ is equal to 1 and less than 1, are preferably used as O/W-emulsifiers, as foam stabilisers for polyurethane foams, demulsifiers in the oil and gas industry, or also as defoamers or in defoaming formulations for e.g. diesel fuels or as coating additive for flow and levelling of paints coating compositions, as additive for anti-blocking, mar resistance, as lubricant or lubricating additive, as tissue softeners or in tissue softener compositions as self-emulsifying alkylene oxide-free softener or as shear stable emulsifier in textile treatment formulations.

If the ratio $R^{21}$ to $R^{22}$ is the same or greater than 1, the use as defoamers, compatibilisators for lipophilic phases, e.g. O/W-emulsions and particularly preferred is the use as demulsifiers in the oil and gas industry for faster and better separation of crude oil and water, coagulant for rubber latex, as additive for anti-blocking, mar resistance, as lubricant or lubricating additive, as tissue softeners or in tissue softener composition as self-emulsifying alkylene oxide-free softener or as shear stable_emulsifier in textile treatment formulations, as foam stabilizers for aqueous foams indetergents, dishwashing liquids and in general-purpose cleaners, cosmetic fatty phases such as creams, plastic and thermoplastic or elastomer additives for hydrophilisation and the improved wettability of thermoplastic or elastomeric surfaces.

It is particularly preferred that polysiloxane (i) according to the invention comprise siloxy units of the formulas:

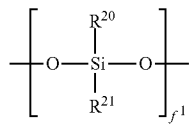

wherein $R^{20}=C_1$ to $C_{22}$-alkyl, fluoroalkyl or aryl, preferably methyl,
$R^{21}$ is as defined above or below, and
$f^1=1$-300, preferably 2 to 200, more preferably 2 to 50, even 3 to 30,

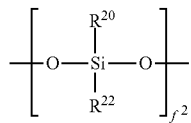

wherein $R^{20}=C_1$ to $C_{22}$-alkyl, fluoroalkyl or aryl, preferably methyl, and
$R^{22}$ is as defined above or below, and
$f^2=1$-300, preferably 2 to 200, more preferably 2 to 50, even 4 to 40,

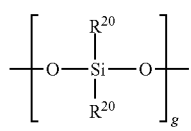

wherein $R^{20}=C_1$ to $C_{22}$-alkyl, fluoroalkyl or aryl, preferably methyl, and
g=0-700,
and

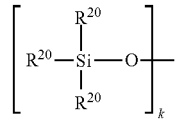

wherein the groups $R^{20}$ can be the same or different and can be selected from $C_1$ to $C_{22}$-alkyl, fluoro-substituted $C_1$ to $C_{22}$-alkyl and aryl, preferably methyl and k=2.

Accordingly, polysiloxane (i) according to the invention preferably are linear trimethylsilyl end-stopped polysiloxane compounds.

In further preferred embodiments of polysiloxane (i) according to the invention at least one, several or all of the following definitions are fulfilled in each case: $R^4$, $R^5$, $R^6$, $R^7$, $R^8$ and $R^9$ are selected from: $C_1$ to $C_{10}$-alkyl, which, if necessary, can be substituted with 1 to 13 fluoro atoms, and aryl, and $R^{10}$ is selected from $R^{11}$, $R^{16}$ and $R^{17}$, and optionally in addition $R^{18}$ may be present as $R^{10}$
Z=a bivalent or trivalent straight-chained, cyclic or branched, saturated or unsaturated $C_2$ to $C_{10}$-hydrocarbon group, which can comprise —O— groups and can be substituted by one or more OH groups,
g=10 to 700, preferably 10 to 200, preferably 10 to 150, preferably 20 to 150, preferably 30 to 150, preferably 30 to 100,
f1=1 to 200, preferably 1 to 100, preferably 1 to 50, preferably 1 to 30, preferably 3 to 30, preferably 5 to 30,
f2=1 to 200, preferably 1 to 100, preferably 1 to 50, preferably 1 to 30, preferably 3 to 30, preferably 5 to 30,
h=0 to 5 and preferably 0,
i1=0 to 5 and preferably 0,
i2=0 to 5 and preferably 0,
l=0 to 5 and preferably 0,
f1+f2+g+h+i1+i2+j1+j2+k+l=10 to 500, preferably 10 to 200, preferably 10 to 150, preferably 20 to 150, preferably 30 to 150, preferably 30 to 100.

In further preferred embodiments of polysiloxane (i) according to the invention one, several or all of the following definitions are fulfilled in each case: $R^4$, $R^5$, $R^6$, $R^7$, $R^8$ and $R^9$ are selected from: $C_1$ to $C_6$-alkyl, which, if necessary, can be substituted with 1 to 13 fluoro atoms, phenyl,
Z=a bivalent or trivalent straight-chained, cyclic or branched, saturated or unsaturated $C_2$ to $C_6$-hydrocarbon group, which can comprise one or more —O— groups and can be substituted by one or more OH groups,
y=1,
$R^{12}$=a straight chained, cyclic or branched, saturated or unsaturated hydrocarbon group with up to 30 carbon atoms, which can comprise one or more groups selected from —O—, —NH—, —NR$^{13}$—, —C(O)— and can be substituted by one or more OH groups, wherein $R^{13}$ is as defined above.

In further preferred embodiments of polysiloxane (i) according to the invention, at least one, several or all of the following definitions are fulfilled in each case:
$R^4$, $R^5$, $R^6$, $R^7$, $R^8$ and $R^9$ are each independently selected from methyl, $R^{21}$ and $R^{22}$, wherein $R^{21}$ and $R^{22}$ is each defined as above,
Z=—CH$_2$CH$_2$CH$_2$—O—CH$_2$—, —CH$_2$CH$_2$CH$_2$—,

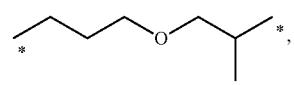

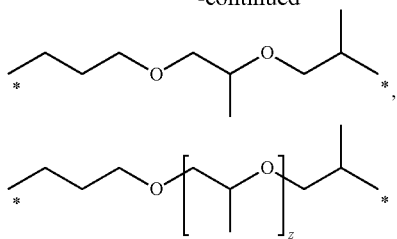

z=1 to 4,
(wherein * marks a bond in each case)
—CH=CH$_2$CH$_2$—, —CH=CH$_2$CH$_2$CH$_2$—,

wherein the bond to the silicon takes places in the 2-position.
x=1.
Particularly
R$^{20}$=C$_1$ to C$_6$-alkyl, fluoroalkyl or phenyl,
Z=bivalent straight-chained, cyclic or branched, saturated or unsaturated C$_1$ to C$_8$-hydrocarbon group, which can comprise one or more —O—, —NH—,

—C(O)— groups, and can be substituted by one or more OH groups,
Especially preferred are
R$^{20}$=methyl,
—Z—=

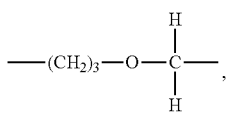

particularly in the R$^{16}$=—Z-E$^2$ version, Z can also be selected from the cyclic structures which are derived from cyclic epoxides, such as

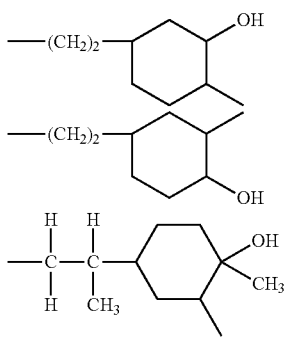

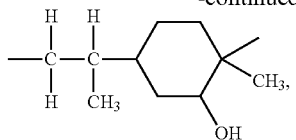

According to the invention, polysiloxane (i) is preferably produced by the following processes, which are characterized in that
(a) an epoxy functional polysiloxane is reacted with one or more, preferably more carboxylic acids and, if necessary, subsequently with primary or secondary amines,
(b) an epoxy functional polysiloxane is reacted with one or more, preferably more carboxylic acids and carboxylic acid anhydrides, wherein the carboxylic acid anhydrides, if necessary, are partially esterified by the addition of monovalent or polyvalent alcohols, and, if necessary, also subsequently with primary or secondary amines,
(c) a SiH functional polysiloxane is reacted with
  (i) one or more mono-functional olefinic or acetylenic unsaturated ethers of glycerine or of glycerine oligomers whose hydroxyl groups, if necessary, can be silylated and/or acetalised and/or ketalised and/or esterified, and
  (ii) one or more esters of fatty acids with unsaturated alcohols,
(d) amino functional polysiloxanes are esterified with carboxylic acids or reacted with epoxy functional compounds.

More specifically the following synthetic pathways are available:
(a) a saturated or unsaturated epoxy functional polysiloxane is reacted with a mixture, containing short chained, preferably hydroxy functionalized, carboxylic acids and long chained, preferably hydroxy free, carboxylic acids, and optionally afterwards with primary or secondary amines,
(b) a saturated or unsaturated epoxy functional polysiloxane is reacted with a mixture, containing short chained, preferably hydroxy functionalized, carboxylic acids and long chained, preferably hydroxy free, carboxylic acids, and optionally afterwards with primary or secondary amines, wherein the carboxylic acids are obtained by partial esterification or amidation of carboxylic acid anhydrides with corresponding alcohols or amines,
(c) a saturated or unsaturated epoxy functional polysiloxane is reacted with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(d) a SiH functionalized polysiloxane is reacted with
  one or more than one monofunctional acetylenically unsaturated ether of glycerol or glycerol oligomers, optionally having silylated, acetylated, ketalized or esterified OH groups,
  and
  one or more than one ester of fatty acids with olefinically or acetylenically unsaturated alcohols (e) a SiH functionalized polysiloxane is reacted with
one or more than one monofunctional olefinically unsaturated ether of glycerol or glycerol oligomers, optionally having silylated, acetylated, ketalized or esterified OH groups,
and
one or more than one ester of fatty acids with acetylenically unsaturated alcohols (f) a SiH functionalized polysiloxane is reacted with
one or more than one monofunctionally unsaturated alkyne or alkene and one or more than one monofunctional olefinically or acetylenically unsaturated epoxide
and subsequently
with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (g) a SiH functionalized polysiloxane is reacted with
one or more than one monofunctionally unsaturated alkyne and one or more than one monofunctional olefinically or acetylenically unsaturated epoxide
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (h) a SiH functionalized polysiloxane is reacted with
one or more than one monofunctionally unsaturated alkyne or alkene and one or more than one monofunctional olefinically or acetylenically unsaturated epoxide and one or more than one olefinically or acetylenically unsaturated fatty acid ester
and subsequently
with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (i) a SiH functionalized polysiloxane is reacted with
one or more than one monofunctional olefinically or acetylenically unsaturated epoxide and one or more than one olefinically or acetylenically unsaturated fatty acid ester
and subsequently
with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (j) a SiH functionalized polysiloxane is reacted with
one or more than one monofunctionally unsaturated alkyne or alkene and one or more than one monofunctional olefinically or acetylenically unsaturated epoxide and one or more than one olefinically or acetylenically unsaturated fatty acid ester
and subsequently
with short chained, preferably hydroxy functionalized, carboxylic acids, and optionally afterwards with primary or secondary amines, wherein optionally the carboxylic acids can be obtained by partial esterification or amidation of carboxylic acid anhydrides with corresponding alcohols or amines, (k) a SiH functionalized polysiloxane is reacted with
one or more than one monofunctional olefinically or acetylenically unsaturated epoxide and one or more than one olefinically or acetylenically unsaturated fatty acid ester
and subsequently
with short chained, preferably hydroxy functionalized, carboxylic acids, and optionally afterwards with primary or secondary amines, wherein optionally the carboxylic acids can be obtained by partial esterification or amidation of carboxylic acid anhydrides with corresponding alcohols or amines, (l) a SiH functionalized polysiloxane is reacted with
one or more than one monofunctionally unsaturated alkyne or alkene and one or more than one monofunctional olefinically or acetylenically unsaturated epoxide and one or more than one olefinically or acetylenically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (m) a SiH functionalized polysiloxane is reacted with
one or more than one monofunctionally unsaturated alkyne or alkene and one or more than one monofunctional olefinically unsaturated epoxide and one or more than one acetylenically unsaturated fatty acid ester and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (n) a SiH functionalized polysiloxane is reacted with
one or more than one monofunctional acetylenically unsaturated epoxide and one or more than one acetylenically or olefinically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (o) a SiH functionalized polysiloxane is reacted with
one or more than one monofunctional olefinically unsaturated epoxide and one or more than one acetylenically unsaturated fatty acid ester
and subsequently
with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
(p) an aminofunctional polysiloxane is reacted with short chained and/or long chained carboxylic acid esters, lactones, carboxylic acid halides or carboxylic acid silyl esters,
(q) an aminofunctional polysiloxane is reacted with short chained and/or long chained alkyl or aryl substituted carbonates, and
(r) an aminofunctional polysiloxane is reacted with short chained and/or long chained alkyl substituted epoxides Further details of the foregoing processes for making polysiloxane (i) are described in U.S. Patent Publication US 2012/0289649 the entire contents of which are incorporated by reference herein.

The amount of polysiloxane (i) that generally used in the compositions can be from 0.05% to 10% by weight based on the total weight of the oil-in-water emulsion composition, more specifically, from 0.1% to 5% by weight based on the total weight of the oil-in-water emulsion composition, and most specifically from 0.5% to 3% by weight based on the total weight of the oil-in-water emulsion composition.

Polymeric Aqueous Thickener (ii)

Polymeric aqueous thickener (ii) can be crosslinked polyacrylate polymers, polyacrylamides, copolymers, any anionic or cationic crosspolymer which can produce a yield point in water.

Examples of such polymeric thickeners are carbopol grades from Lubrizol, carbopol 1382, ammonium acryloyldimethyltaurate/VP copolymer (aristoflex AVC), ammonium acryloyldimethyltaurate/beheneth-25 methacrylate crosspolymer (Aristoflex HMB), carboxyvinyl polymers, the Pemulen products (acrylate/C10-C30-alkylacrylate copolymer); polyacrylamides, for instance the crosslinked copolymers Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) by Hoechst under the trade name "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

The amount of polymeric aqueous thickener (ii) that generally used in the compositions can be from 0.05% to 10% by weight based on the total weight of the oil-in-water emulsion composition, more specifically, from 0.1% to 5% by weight based on the total weight of the oil-in-water emulsion composition, and most specifically from 0.2% to 3% by weight based on the total weight of the oil-in-water emulsion composition.

Oil (iii)

Oil (iii) can comprise an oil or combinations of two or more oils and also further oil-compatible cosmetic raw materials. Oils, which are used in cosmetics differ in their polarity. These can, according to the literature (Cosmetology—Theory and Practice; Volume 3, page 31, Table 10.2; Editors: K. Schrader, A. Domsch; Verlag für chemische Industrie, 2005), be described by their surface tension (also defined as polarity index). A particular characteristic of the polysiloxane compounds according to the invention is that, in this connection, they are capable of stabilising emulsions with a great range of oil polarities. In this connection the preferred oil polarities represented by the polarity index lie in a range of between 4 and 55 mN/m, with the range between 13 and 39 mN/m being particularly preferred. In this connection it is self-evident that the values of the oil polarities lie in the preferred or more preferred range and can be achieved by mixing or blending two or more components. The following materials are named as possible components for the oil phase, by way of example but not limiting, wherein the materials can be introduced singly or in combinations of several components. Triglycerides are, for example, avocado oil, peanut oil, hydrogenated peanut oil, oat oil, mink oil, olive oil, castor oil, hydrogenated caster oil, shea butter oil, soy oil, sunflower oil, sesame oil, peach stone oil, wheat germ oil, macadamia nut oil and oenothera biennis oil.

Silicones such as volatile linear and cyclic polydimethyl siloxane (hexamethyl disiloxane, ethyl-, propyl and butyl disiloxane, dipropyl- and dibutyl disiloxane, octamethyl disiloxane, octamethyl trisiloxane, pentamethyl tetrasiloxane, dodecamethyl pentasiloxane, various ethyl and diethyltrisiloxanes, various propyl- and dipropyl trisiloxanes, various butyl trisiloxanes, various pentyl trisiloxanes, various hexyl trisiloxanes, cyclotetrasiloxanes, cyclopentasiloxanes, cyclohexasiloxanes, cycloheptasiloxanes and further variations), dimethicone (viscosity 3-100 kPa·s at 25° C. as well as blends of the different viscosities and solutions of dimethicones in volatile silicones and hydrocarbons), phenyl modified silicones (phenyltrimethicones and phenyldimethicones with different viscosities as well as blends thereof), alkyl- and aryl modified silicones (caprylylmethicones, stearyl-, cetyl-, cetearyl-, C26-C28-alkyl C30-C45-alkyl methicones and dimethicones, phenylpropyldimethylsiloxysilicate), polyether modified silicones (INCI: PEG-x/PPG-y dimethicones), amino functional silicones (amo-dimethicones), fluoroalkyl modified silicones, silicone resins (trimethylsiloxysilicate, polymethylsilsesquioxanes, diisostearyl trimethylolpropane siloxysilicates and trifluoropropyl/trimethylsiloxysilicates), silicone acrylates (dimethicone PEG-8 Polyacrylates) and silicone elastomers and silicone crosspolymers (dimethicone/vinyl dimethicone crosspolymer, C30-C45-alkyl cetearyl dimethicone crosspolymer, cetearyl dimethicone crosspolymer, dimethicone crosspolymer, cetearyl dimethicone crosspolymer, dimethicone/PEG-10/15 crosspolymer, PEG-15/lauryl dimethicone crosspolymer, PEG-10/lauryl dimethicone crosspolymer, dimethicone/polyglycerine-3 crosspolymer, lauryl dimethicone/polyglycerine-3 crosspolymer and dimethicone/vinyltrimethyl siloxysilicate crosspolymer).

Hydrocarbons such as for example paraffin oils with various viscosities, petroleum jelly, paraffins (hard and soft), microcrystalline waxes, ozocerites, ceresin, squalenes, squalanes and volatile, linear and/or branched hydrocarbons with 5 to 20 carbon atoms.

Fatty alcohols as consistency regulators such as, for example, lauryl-, myristyl-cetyl-, oleyl- and stearyl alkohol, and mono- and diglycerides of fatty acids.

Natural waxes and fats and those based on natural products such as Japanese wax, lanolin, cocoa butter, cetyl palmitate, beeswax (natural and synthetic), carnauba wax, candelilla wax and jojoba oil.

Fatty acid esters of monoalcohols such as isopropyl myristates, isopropyl palmitates, isopropyl stearates, oleyl oleates, decyl oleates and cetearyl ethylhexanoates.

Nonvolatile oils which can be used in the invention include, but are not limited to, monoesters, diesters, triesters, mixed aliphatic and/or aromatic, polar oils such as: hydrocarbon-based oils of animal origin, such as perhydrosqualene; hydrocarbon-based plant oils such as liquid triglycerides of fatty acids and of glycerol, in which the fatty acids may have varied chain lengths, these chains being linear or branched, and saturated or unsaturated; these oils can be chosen, for example, from wheat germ oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quina oil, olive oil, rye oil, safflower oil, candlenut oil, passion flower oil, musk rose oil and caprylic/capric acid triglycerides such as those sold by the company Stéarineries Dubois or those sold under the names MIGLYOL 810, 812 and 818 by the company Dynamit Nobel; natural or synthetic esters of formula R1COOR2, wherein R1 is a higher fatty acid residue comprising 7 to 19 carbon atoms, and R2 is a branched hydrocarbon-based chain comprising 3 to 20 carbon atoms, such as, for example, purceilin oil (cetostearyl octanoate), isopropyl myristate and alkyl or polyalkyl octanoates, decanoates or ricinoleates; synthetic ethers of formula R3COR4, wherein R3 is a C3 to C19 alkyl radical, and R4 is a C3 to C20 alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctylcyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate; primary, secondary or tertiary amines such as triethanolamine; and mixtures thereof. In one embodiment, synthetic esters such as isopropyl myristate are used.

Aqueous Phase

Addition of an emulsion-forming amount of water or water containing and/or more optional components dissolved and/or suspended therein to the oil-in-water emulsion-forming composition herein provides an oil-in-water emulsion composition. The amount of water added to the oil-in-water emulsion-forming composition can vary widely, i.e., to provide an emulsion containing from 10 to 90 weight percent water, advantageously from 20 to 80 weight percent water and particularly from 30 to 70 weight percent water.

Optional Components

The oil-in-water emulsion composition of the present invention may contain one or more active ingredients in its oil and/or water phase.

The active ingredients useful herein can be categorized by their therapeutic benefit or their postulated mode of action. However, it is to be understood that the active ingredients useful herein can, in some instances, provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

The oil-in-water emulsion composition of the present invention may contain Anti-Acne Actives. Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

The oil-in-water emulsion composition of the present invention may contain Antimicrobial and Antifungal Actives: Examples of antimicrobial and antifungal actives include .beta.-lactam drugs, quinolone drugs, ciprofloxacin, norfloxacin, tetracycline, erythromycin, amikacin, 2,4,4'-trichloro-2'-hydroxy diphenyl ether, 3,4,4'trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

The oil-in-water emulsion composition of the present invention may contain shine enhancing agents. Suitable shine enhancing agents include those compounds having a refractive index ranging from 1.45 to 1.60. Examples thereof include, but are not limited to, phenylated silicones such as phenyl trimethicone, and trimethyl pentaphenyl trisiloxane. Examples of suitable phenylated silicones include, those commercialized by Momentive such as Silshine 121, or Wacker Silicones such as BELSIL PDM 20, BELSIL PDM 200, a BELSIL PDM 1000. Additional examples of suitable shine enhancing agents include, but are not limited to, polycyclopentadiene, poly(propylene glycol)dibenzoate (nD=1.5345), aminopropyl phenyl trimethicone (nD=1.49-1.51), pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

The oil-in-water emulsion composition of the present invention may also contain: antipollution agents and/or free-radical scavengers; depigmenting agents and/or propigmenting agents; antiglycation agents; NO-synthase inhibitors; agents for stimulating the synthesis of dermal or epidermal macromolecules and/or for preventing their degradation; agents for stimulating fibroblast proliferation; agents for stimulating keratinocyte proliferation; muscle relaxants; tensioning agents; desquamating agents; moisturizers; anti-inflammatory agents; agents acting on the energy metabolism of cells; insect repellants; and substance P or CGRP antagonists.

Furthermore, the oil-in-water emulsion composition of the present invention may contain film-formers. Film-formers are often incorporated into sunscreen compositions to ensure even coverage of the UV filters and can be used to render the composition water resistant. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and mixtures thereof. In some cases, the film former is acrylates/$C_{12}$-$C_{22}$ alkylmethacrylate copolymer sold under the tradename Allianz OPT® by ISP.

Many of the common film-forming polymers included in sunscreen compositions are not soluble in ethanol (such as PVP/Eicosene copolymer). A common film-former employed in ethanol based sunscreen products is Dermacryl LT or Dermacryl 79 marketed by Akzo Nobel ONO Name: acrylates/octylacrylamide copolymner). Dermacryl LT (CAS Number: 80570-62-3) is a hydrophobic, high molecular weight carboxylated acrylic copolymer. It functions as a film-former in a broad range of cosmetic formulations, imparting waterproofing, increased occlusivity and decreased rub-off of actives.

The oil-in-water emulsion composition of the present invention may contain emulsifiers. For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose. The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tego-care 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the present disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglycoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tego-care CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BBS, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The oil-in-water emulsion composition of the present invention may contain UV Filters. UV filters are substances, which selectively absorb UVA and/or UVB radiation. Depending on the requirement profile, UV filters can be combined together and/or with micro pigments. Lists of suitable UV filters can be found in the "International Cosmetic Ingredient Dictionary and Handbook" Eleventh Edition 2006, Volume 3, page 2881 and "Cosmetology—Theory and Practice" Volume 3, pages 161-168; Editors: K. Schrader, A. Domsch; Verlag für Chemische Industrie, 2005.

The oil-in-water emulsion composition of the present invention may contain sunscreen actives. Examples thereof include, but are not limited to, butyl methoxydibenzoylmethane; anthranilates; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. Nos. 5,237,071, 5,166,355, GB 2 303 549, DE 197 26 184 and EP 893 119; benzoxazole derivatives such as those described in patent applications EP 0 832 642; EP 1 027 883, EP 1 300 137 and DE 101 62 844; screening polymers and screening silicones such as those described especially in patent application WO 93/04665; dimers derived from α-alkylstyrene, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and sunscreens described in "Sunscreens, Regulations and Commercial Development", 3$^{rd}$ edition, Nadim A. Shaa th editor, Informa Healthcare, London, UK, 2011, and mixtures thereof.

As examples of organic photoprotective agents, mention may be made of those denoted hereinbelow under their INCI name: Butyl methoxydibenzoylmethane sold by A&E Connock (Perfumery & Cosmetics) LTD., also known as Avobenzone and also sold under the names "Eusolex 9020" sold by Merck KGaA/EMD Chemicals Inc., "Neo Heliopan" sold by Symrise, "Parsol 1789" sold by DSM Nutritional Products and "Oristar ABZ" sold by Orient Stars LLC.

Para-Aminobenzoic Acid Derivatives: PABA, Ethyl PABA, Ethyl dihydroxypropyl PABA, Ethylhexyl dimethyl PABA sold in particular under the name "Escalol 507" by ISP, Glyceryl PABA, PEG-25 PABA sold under the name "Uvinul P25" by BASF.

Salicylic Derivatives: Homosalate sold under the name "Eusolex HMS" by Rona/EM Industries, Ethylhexyl salicylate sold under the name "Neo Heliopan OS" by Haarmann and Reimer, Dipropylene glycol salicylate sold under the name "Dipsal" by Scher, TEA salicylate sold under the name "Neo Heliopan TS" by Haarmann and Reimer.

β,β-Diphenylacrylate Derivatives: Octocrylene sold in particular under the trade name "Uvinul N539" by BASF, Etocrylene sold in particular under the trade name "Uvinul N35" by BASF.

Benzophenone Derivatives: Benzophenone-1 sold under the trade name "Uvinul 400" by BASF, Benzophenone-2 sold under the trade name "Uvinul D50" by BASF, Benzophenone-3 or Oxybenzone sold under the trade name "Uvinul M40" by BASF, Benzophenone-4 sold under the trade name "Uvinul MS40" by BASF, Benzophenone-5, Benzophenone-6 sold under the trade name "Helisorb 11" by Norquay, Benzophenone-8 sold under the trade name "Spectra-Sorb UV-24" by American Cyanamid, Benzophenone-9 sold under the trade name "Uvinul DS-49" by BASF, Benzophenone-12 Diethylaminohydroxybenzoylhexyl benzoate sold under the trade name "Uvinul A Plus" by BASF.

Benzylidenecamphor Derivatives: 3-Benzylidenecamphor manufactured under the name "Mexoryl SD" by Chimex, 4-Methylbenzylidenecamphor sold under the name "Eusolex 6300" by Merck, Benzylidenecamphorsulfonic acid manufactured under the name "Mexoryl SL" by Chimex, Camphor benzalkonium methosulfate manufactured under the name "Mexoryl SO" by Chimex, Terephthalylidenedicamphorsulfonic acid manufactured under the name "Mexoryl SX" by Chimex, Polyacrylamidomethylbenzylidenecamphor manufactured under the name "Mexoryl SW" by Chimex.

Phenylbenzimidazole Derivatives: Phenylbenzimidazolesulfonic acid sold in particular under the trade name "Eusolex 232" by Merck, Disodium phenyl dibenzimidazole tetrasulfonate sold under the trade name "Neo Heliopan AP" by Haarmann and Reimer.

Phenylbenzotriazole Derivatives: Drometrizole trisiloxane sold under the name "Silatrizole" by Rhodia Chimie, Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives: -Bis(ethylhexyloxyphenol) methoxyphenyl triazine sold under the trade name "Tinosorb S" by Ciba-Geigy, Ethylhexyltriazone sold in particular under the trade name "Uvinul T150" by BASF, Diethylhexylbutamidotriazone sold under the trade name "Uvasorb HEB" by Sigma 3V, 2,4,6-tris(diisobutyl 4'-aminobenzalmalonate)-s-triazine.

Anthranilic Derivatives: Menthyl anthranilate sold under the trade name "Neo Heliopan MA" by Haarmann and Reimer.

Imidazoline Derivatives: Ethylhexyldimethoxybenzylidenedioxoimidazoline propionate.

Benzalmalonate Derivatives: Polyorganosiloxane containing benzalmalonate functions, for instance Polysilicone-15, sold under the trade name "Parsol SLX" by Hoffmann LaRoche.

4,4-Diarylbutadiene Derivatives: 1,1-Dicarboxy(2,2'-dimethylpropyl)-4,4-diphenyl-butadiene.

Benzoxazole Derivatives: 2,4-bis[5-(1-dimethylpropyl)benzoxazol-2-yl(4-phenyl)imino]-6-(2-ethylhexyl)imino-1,3,5-triazine sold under the name Uvasorb K2A by Sigma 3V, and mixtures thereof.

Examples of mineral photoprotective agents are chosen from pigments and even more preferably nanopigments (mean size of the primary particles: generally between 5 nm and 100 nm and preferably between 10 nm and 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, poly-ethylene, silicones, proteins (collagen or elastin), alkanolamines, silicon oxides, metal oxides, sodium hexametaphosphate, alumina or glycerol.

The treated nanopigments may more particularly be titanium oxides treated with: silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide, alumina and aluminium stearate, such as the product "Microtitanium Dioxide MT 100 T" from the company Tayca, alumina and aluminium laurate, such as the product "Microtitanium Dioxide MT 100 S" from the company Tayca, iron oxides and iron stearate, such as the product "Microtitanium Dioxide MT 100 F" from the company Tayca, silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

Other titanium oxide nanopigments treated with a silicone are preferably $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimethylhydrogenosiloxane and for which the mean size of the elementary particles is 25 nm, such as the product sold under the trade name "Microtitanium Dioxide USP Grade Hydrophobic" by the company Color Techniques.

The uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide nanopigments are, for example: those sold under the name "Z-Cote" by the company Sunsmart; those sold under the name "Nanox" by the company Elementis; those sold under the name "Nanogard WCD 2025" by the company Nanophase Technologies.

The coated zinc oxide nanopigments are, for example: those sold under the name "Zinc Oxide CS-5" by the company Toshibi (ZnO coated with polymethylhydrogenosiloxane); those sold under the name "Nanogard Zinc Oxide FN" by the company Nanophase Technologies (as a 40% dispersion in Finsolv TN, $C_{12}$-$C_{15}$ alkyl benzoate); those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane); those sold under the name "NFD Ultrafine ZNO" by the company Daikin (ZnO coated with perfluoroalkyl phosphate and copolymer based on perfluoroalkylethyl as a dispersion in cyclopentasiloxane); those sold under the name "SPD-Z1" by the company Shin-Etsu (ZnO coated with silicone-grafted acrylic polymer, dispersed in cyclodimethylsiloxane); those sold under the name "Escalol Z100" by the company ISP (alumina-treated ZnO dispersed in an ethylhexyl methoxycinnamate/PVP-hexadecene/methicone copolymer mixture); those sold under the name "Fuji ZNO-SMS-10" by the company Fuji Pigment (ZnO coated with silica and polymethylsilsesquioxane); those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide" by the company Rhone-Poulenc.

The uncoated iron oxide nanopigments are sold, for example, by the company Arnaud under the names "Nanogard WCD 2002 (FE 45B)", "Nanogard Iron FE 45 EL AQ", "Nanogard FE 45R AQ" and "Nanogard WCD 2006 (FE 45R)" or by the company Mitsubishi under the name "TY-220".

The coated iron oxide nanopigments are sold, for example, by the company Arnaud under the names "Nanogard WOO 2008 (FE 455 FN)", "Nanogard WCD 2009 (FE 45B 556)", "Nanogard FE 45 BL 345" and "Nanogard FE 45 BL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The amount of oil (iii) that generally used in the compositions can be from 1% to 60% by weight based on the total weight of the oil-in-water emulsion composition, more specifically, from 10% to 60% by weight based on the total weight of the oil-in-water emulsion composition, and most specifically from 20% to 60% by weight based on the total weight of the oil-in-water emulsion composition.

Additional optional components that can be incorporated in the oil-in-water emulsion composition of the invention include organic solvent, surfactant, colorant, filler, reinforcing agent, adhesion promoter, UV stabilizer, color stabilizer, wetting agent, flow and leveling additive, and the like.

Organic solvents are used to lower the viscosity and improve the flow properties of the oil-in-water emulsion compositions, which are especially useful when the oil-in-water emulsion composition is used as a coating. A variety of solvents may be mentioned as exemplary, for example, alcohols, glycols, triols, polyols, glycol ethers, esters, ketones, hydrocarbon, and the like.

Representative and non-limiting examples of specific solvents include mono-alcohols, such as methanol, ethanol, 1-propanol, 2-propanol (i-propanol), 2-methyl-1-propanol (i-butanol), 2-methyl-2-propanol (tert-butanol), 1-butanol, 2-butanol, 2-methyl-1-butanol, 2-methyl-2-butanol, 2,2-dimethyl-1-propanol, 1-pentanol, 2-pentanol, 4-methyl-2-pentanol; glycols such as propylene glycol, 1,3-butanediol, 1,4-butane diol, 2-methyl-1,3-propanediol, 2-methyl-2,4-pentanediol (hexylene glycol), diethylene glycol, triethylene glycol, tetraethylene glycol, poly(ethylene glycol), dipropylene glycol, tripropylene glycol, poly(propylene glycol), 1,5-pentanediol, esterdiol 204, 2,2,4-trimethylpentanediol, 2-ethyl-1,3-hexanediol, glycerol, glycerol ethoxylate, glycerol ethoxylate-co-propoxylate triol, glycerol propoxylate, pentaerythritol; glycol ethers such as 1-methoxy-2-propanol (propylene glycol methyl ether), 1-ethoxy-2-propanol, 1-propoxy-2-propanol, 1-butoxy-2-propanol, 2-methoxyethanol, 2-ethoxyethanol, 2-propoxyethanol, 2-butoxyethanol, 2-(2-methoxyethoxy)ethanol, 2-(2-ethoxyethoxy)ethanol, 2-(2-propoxyethoxy)ethanol, 2-(2-butoxyethoxy) ethanol (butyl carbitol), di(propylene glycol) butyl ether, tri(ethylene glycol)monomethyl ether, tri(ethylene glycol) monoethyl ether, tri(ethylene glycol) monobutyl ether, poly (ethylene glycol) methyl ether, poly(ethylene glycol) dimethylether, poly(ethylene glycol-co-propylene glycol), poly (ethylene glycol-co-propylene glycol)monobutyl ether, poly (propylene glycol)monobutyl ether, di(propylene glycol) dimethylether; esters including methyl acetate, ethyl acetate, ethyl lactate, 2-methoxyethyl acetate, 2-ethoxyethyl acetate, 2-butoxyethyl acetate, 2-(2-methoxyethoxy)ethyl acetate, 2-(2-ethoxyethoxy)ethyl acetate, 2-(2-butoxyethoxy)ethyl acetate, glycol diacetate, triethylene glycol diacetate, propylene glycol methyl ether acetate (1-methoxy-2-propanol acetate), propylene glycol ethyl ether acetate, ketones including acetone, methyl ethyl ketone, 2,4-pentane dione, diacetone alcohol and hydrocarbons including toluene, xylene, naptha, mineral spirits, hexane, heptane, cyclohexane and mixtures thereof.

In certain embodiments, the solvent can be present in the oil-in-water emulsion composition of the invention in an amount ranging from 1 to 80 percent by weight, advantageously from 10 to 30 percent by weight, and in some embodiments, from 10 to 25 percent by weight, based on the total weight of the oil-in-water emulsion composition.

Surfactants may be used to aid in the wetting and leveling of the oil-in-water emulsion compositions of the invention. Useful surfactants include nonionic, cationic, anionic, amphoteric and/or zwitterionic surfactants. The surfactants are typically hydrocarbon-based, silicone-based or fluorocarbon-based. Useful surfactants having short chain hydrophobes. Other useful surfactants include alkoxylates, especially ethoxylates, containing block copolymers including copolymers of ethylene oxide, propylene oxide, butylene oxide, and mixtures thereat alkylarylalkoxylates, especially ethoxylates or propoxylates and their derivatives including alkyl phenol ethoxylate; arylarylalkoxylates, especially ethoxylates or propoxylates, and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and mixtures thereof.

Representative, non-limiting examples of surfactants include alkyl acetylenic dials sold by Air Products under the trade name SURFONYL®, pyrrilodone-based surfactants sold by ISP under the trade name SURFADONE-LP® 100, 2-ethyl hexyl sulfate, isodecyl alcohol ethoxylates sold by Rhodia under the trade name RHODASURF® DA 530, ethylene diamine alkoxylates sold by BASF under the trade name TETRONICS®, ethylene oxide/propylene oxide copolymers sold by BASF under the trade name PLURONICS®, and diphenyl ether Gemini type surfactants sold by Dow Chemical Corporation under the trade name DOWFAX®.

In general, the oil-in-water emulsion composition herein can contain the optional surfactant(s) in an amount of from 0.01 to 5 weight percent, advantageously from 0.05 to 2 weight percent and in certain embodiments, from 0.1 to 1 weight percent based on the total weight of the oil-in-water emulsion composition.

The oil-in-water emulsion composition of the invention can include a colorant. As used herein, the term "colorant" means any substance that imparts color and/or other opacity and/or other visual effect to the polymer. The colorant can be added to the oil-in-water emulsion composition in any suitable form such as discrete particles, dispersions, solutions, flakes, etc. A single colorant or a mixture of two or more colorants can be used in the oil-in-water emulsion composition of the invention.

Useful colorants include pigments, dyes and tints such as those used in the paint industry and/or listed in the Dry Color Manufacturers Association (DCMA), as well as special-effect materials. A useful type of colorant can be a finely divided solid powder that is insoluble but wettable under the conditions of use. A colorant can be organic or inorganic and can be agglomerated or non-agglomerated. Colorants can be incorporated into the oil-in-water emulsion composition by use of a grinding vehicle such as an acrylic grinding vehicle the use of which is familiar to those skilled in the art.

Illustrative useful pigments and pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triaryl-carbonium, quinophthalone pigments, diketo pyrrolo pyrrole red ("DPPBO red"), titanium dioxide, carbon black and mixtures thereof. The terms "pigment" and "colored filler" can be used interchangeably.

Useful dyes include, but are not limited to, those that are solvent and/or aqueous based such as phthalo green or blue, iron oxide, bismuth vanadate, anthraquinone, perylene, aluminum and quinacridone.

Useful tints include, but are not limited to, pigments dispersed in water-based or water miscible carriers such as AQUA-CHEM® 896 commercially available from Degussa, Inc., CHARISMA COLORANTS® and MAX-ITONER INDUSTRIAL COLORANTS® commercially available from Accurate Dispersions division of Eastman Chemical, Inc.

In general, the colorant can be present in the oil-in-water emulsion composition in any amount that is sufficient to impart the desired visual and/or color effect. The colorant can comprise from, for example, 1 to 65 weight percent of the oil-in-water emulsion composition, such as from 3 to 40 weight percent or 5 to 35 weight percent thereof based on the total weight of the oil-in-water emulsion composition.

The oil-in-water emulsion composition of the invention can include a filler. The filler can be any inorganic or organic filler that reinforces and/or extends the oil-in-water emulsion composition. Useful fillers include, for example, reinforcing fillers such as carbon black, fumed silica, precipitated silica, clays, talc, aluminum silicates, metal oxides and hydroxides, and extending fillers such as treated and untreated calcium carbonates, and the like. Fillers can be in the form of powders, particulates, aggregates, agglomerates, platelets, fibers, etc. In one embodiment, one or more fillers are combined with silane coupling agents.

To further improve the physical strength of the oil-in-water emulsion compositions herein, reinforcing carbon black can be used as a main filler resulting in black or darkly colored oil-in-water emulsion compositions. Several commercial grades of carbon black useful in this invention are commercially available such as the Corax® products from Degussa. To obtain colorless translucent oil-in-water emulsion composition, higher levels of fumed silica or precipitated silica can be used as the main filler to the exclusion of carbon black. The surface area of the filler can be more than 20 meters$^2$/gram.

Treated calcium carbonates having particle sizes from 0.07 microns to 4 microns are preferred fillers and are available under several trade names, such as: "Ultra Pflex®" and "Hi Pflex®" from Specialty Minerals; "Winnofil® SPM" and "Winnofil® SPT" from Zeneca Resins; "Hubercarb® 1 Qt", "Hubercarb® 3 Qt" and "Hubercarb® W" from Huber and "Kotomite®" from ECC; "Omyabond® 520", "Omyacarb® 3", "Omyacarb® 5" from Omya, and the like. These fillers can be used either alone or in combination.

The optional fillers can be incorporated in the oil-in-water emulsion composition in an amount of up to 80 weight percent, advantageously in an amount of up to 50 weight percent, and in certain embodiments, in an amount of from 20 weight percent to 50 weight percent based on the total weight of the oil-in-water emulsion composition.

The oil-in-water emulsion composition herein can optionally include plasticizers. Exemplary plasticizers include phthalates, dipropylene and diethylene glycol dibenzoates and mixtures thereof, epoxidized soybean oil, and the like. Useful commercial dioctyl and diisodecyl phthalates include "Jayflex® DOP" and "Jayflex® DIDP" from Exxon Chemical. Dibenzoate plasticizers are available as "Benzoflex® 9-88", "Benzoflex® 50" and "Benzoflex® 400" from Velsicol Chemical Corporation; "Mesamoll®" from Lanxess. The optional plasticizer can represent up to 100 parts by weight per hundred parts of the oil-in-water emulsion composition with up to 40 parts by weight per hundred parts of the oil-in-water emulsion composition being preferred.

Optional antioxidants that can be added to the composition of the invention to provide protection against oxidative change. The quantities in which antioxidants can be used vary within wide limits, for example, from 0.01 to 10 percent by weight and, more particularly, from 0.01 to 3 percent by weight, based on the weight of the oil-in-water emulsion composition.

According to one embodiment of the invention, the color stabilizer is added during the synthetic process to reduce the yellowing of the final oil-in-water emulsion composition product. Representative non-limiting examples of color stabilizers include, for example, triphenyl phosphite, diphenyl-alkyl phosphites, phenyl-dialkyl phosphites, tris(nonylphenyl)phosphite, trilauryl phosphite, trioctadecyl phosphite, distearyl-pentaerythritol diphosphite, tris(2,4-di-tert-butyl-phenyl)phosphite, diisodecyl pentaerythritol diphosphite, bis(2,4-di-tert-butylphenyl)-pentaerythritol diphosphite, bis (2,4-di-cumylphenyl)-pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, bis(2,4-di-tert-butyl-6-methylphenyl)-methyl phosphite, bis(2,4-di-tert-butyl-6-methylphenyl)-ethyl phosphite, 2,2',2"-nitrilo-[triethyltris(3,3',5,5'-tetra-tert-butyl-1,1'-biph-enyl-2,2'-diyl)phosphite], 2-ethylhexyl (3,3',5,5'-tetra-tert-butyl-1,1'-biphenyl-2,2'-diyl)phosphite-.

Examples of commercial available color stabilizers include but are not limited to Doverphos® from Dover Chemical Corporation, such as Doverphos® 4 (TNPP) (trinonylphenol phosphate), Doverphos® 4-HR (TNPP) (trisnonylphenol phosphite+0.75% triisopropanolamine), Doverphos® 4-HR Plus (TNPP) (trisnonylphenol phosphite+1.0% triisopropanolamine), Doverphos® HiPure 4 (TNPP) (trisnonylphenol phosphite 0.1% max. free nonylphenol), Doverphos® HiPure 4-HR (TNPP) [trisnonylphenol phosphite 0.1% max. free nonylphenol (+0.75% triisopropanolamine)], Doverphos® 10 (TPP) (triphenyl phosphate), Doverphos® 10 HR (TPP) (triphenyl phosphite+0.5% triisopropanolamine), Doverphos® 213 (DPP) (diphenyl phosphate), Doverphos® 7 (PDDP) (phenyl diisodecyl phosphate), Doverphos® 8 (DPDP) (diphenyl isodecyl phosphate), Doverphos® 9 (DPIOP) (diphenyl isooctyl phosphate), Doverphos® 11 (tetraphenyl dipropyleneglycol diphosphite), Doverphos® 12 [poly (dipropyleneglycol) phenyl phosphate], Doverphos® 613 [alkyl ($C_{12}$-$C_{15}$)bisphenol A phosphate], Doverphos® 675 [alkyl($C_{10}$)bisphenol A phosphate], Doverphos® 6 (TDP) (triisodecyl phosphate), Doverphos® 49 (TTDP) [tris(tridecyl)phosphate], Doverphos® 53 (TLP) (trilauryl phosphate), Doverphos® 72 [tris(dipropylene glycol) phosphate], Doverphos® 253 (dioleyl hydrogen phosphate).

The oil-in-water emulsion composition of the invention exhibits no significant whitening effect when applied to a water-wet substrate.

The oil-in-water emulsion composition of the invention is highly suitable for use in personal care products, textile treatments, polishing products, gloss enhancements and water resistance treatments.

Active Substances or Active Ingredients for Skincare Products

Suitable active ingredients for the production of oil-in-water emulsions with polysiloxane (i) according to the invention are propolis or propolis wax, which is used because of its antimicrobial and antioxidative effect of the flavonoids comprised therein, Royal Jelly, which is suitable as a nurturing additive because of its high content of vitamins, amino acids, sugars, enzymes and biopeptin, collagen for stabilising the moisture of the stratum corneum, collagen hydrolysate for the improvement of skin and mucous membrane tolerance, elastin hydrolysate (hydrolysed elastin) alone or in combination with soluble collagen for the improvement of skin elasticity by hydration, phytosterols (avocado oil unsaponifiables, soy bean oil unsaponifiables) for a positive effect on the skin's connective tissue, vitamins such as vitamin A (retinol, retinyl acetate, retinyl palmitate and retinyl propionate) for the treatment and prevention of dry, rough, cornified and aging skin and atrophy of the perspiratory glands, beta-carotene which in the form of provitamin A exhibits the same effects as vitamin A, vitamin E (tocopherol, tocopherol acetate and tocopherol nicotinate) because of its antioxidative effect, improvement of the structure of the skin's surface, increase of the moisture-retaining properties of the corneum, the anti-inflammatory effect, acceleration of the epithelisation of superficial wounds, increase in the enzyme activity of the skin and boosting the blood circulation of the skin, pyridoxin or pyridoxin.HCl (vitamin B6) for the treatment of pellagra particularly in combination with essential fatty acids, niacin or niacin amides for the treatment of pellagra and of skin changes caused by deficiency symptoms, biotin (vitamin H) for the treatment of hair loss and anti-seborrhoic vitamin panthenol or d-panthenol and calcium panthenate for the improvement and increase of the moisture-retaining properties of the skin, for the inhibition of inflammation and itching, for the stimulation of epithelisation (accelerated healing of wounds), and for the improvement of the condition of damaged hair, vitamin C (ascorbic acid, sodium ascorbate and ascorbyl palmitate) because of its antioxidative effect and for the reduction of nitrosamine formation, essential fatty acids such as vitamin F (linoleic acid (and) linolenic acid (and) archidonic acid), vitamin-F-glycerol ester (glyceryl linoleic acid (and) glyceryl linolenic acid (and) glyceryl archidonic acid) and Vitamin-F-ethyl ester (ethyl linoleic acid (and) ethyl linolenic acid (and) ethyl archidonic acid) for the treatment of deficiency symptoms caused by a deficiency of linoleic acid such as dry, scaly skin rash, ceramide for the increase of moisture in the stratum corneum, anti-inflammatory substances such as bisabolol, camomile extracts, panthenol, glycyrrhizinic acid, witch hazel extract and certain peptides, ceratene-hardening substances which react with the proteins in the upper skin layers and thus to some extent seal it, such as formaldehyde or but also potassium aluminium sulfate, aluminium hydroxychloride, aluminium lactate, sodium aluminium chlorohydroxy acetate and aluminium circonium tetrachlorohydrate-glycin complex which clog up the capillaries and also the perspiratory glands, antimicrobial substances, hyperemic substances which stimulate blood flow such as essential oils such as mountain pine oil, lavender, rosemary, juniper, horse chestnut extract, birch leaf extract, cornflower extract, ethyl acetate, nettle extract, camphor, menthol, nicotinic acid and derivatives, peppermint oil, eucalyptus oil and turpentine oil, liposomes for increasing skin penetration, glycolipids such as glycerol glyco-lipids, glycosphingolipids (neutral glycosphingolipids, sulfatides and gangliosides) and cerebrosides, lipoproteins and zinc oxide for anti-inflammation.

Micro Pigments

Micro pigments are also called UV-blockers. They are characterized in that they are insoluble in the oil and the aqueous phases of the emulsion and offer UV protection in that they reflect and disperse UV light independently of their size. In this connection attention must also be paid to the fact that that with a decreasing particle size the "whitening" effect of pigment residues on the skin are reduced. Mainly magnesium oxide, calcium carbonate, magnesium carbonate, bentonite, titanium dioxide and zinc oxide are used. Titanium dioxide and zinc oxide are the most frequently used, with the use of zinc oxide being favoured because of its additional anti-inflammatory effect. Of late organic compounds are also used as micro pigments. An example of this is bis-ethylhexyloxyphenyl triazine (Tinosorb S, Ciba). When using micro pigments it is important that they are easily dispersed in the incorporated phase in order to ensure an ideal covering of the skin, which then results in a more effective UV protection. For this the above-mentioned pigments are also used as surface-treatment materials or as pre-dispersions. For the production of dispersions all substances, which have already been mentioned above as components for the oil phase or the aqueous phase can be used. The surface treatment also results from these substances. Furthermore, for the surface treatment dimethicones, simethicone and cylic silicones and emulsions thereof, hexamethyldisiloxane, hexamethyldisiloxane, alkyl- and aryl-functionalised silicones with alkyl- or aryl groups comprising 2 to 50 C-atoms, methyl-, alkyl- and aryl-functionalised alkoxy or halogen silanes with alkyl- or aryl groups comprising 2 to 50 C-atoms or polyether-modified silicones are frequently used.

The micro pigments can be introduced singly or also in combinations. A combination with the following UV filters for optimising the UV protection is also possible.

Skin Tanning Agents

In this connection, examples of substances which tan the skin to be named are dihydroxyacetone, DHA and walnut extract.

Skin Bleaching Agents

Skin bleaching agents are used for the treatment of age spots or freckles. Active substances which can be used for producing cosmetic compositions with in accordance with the invention are hydroquinone, ascorbic acid, various peroxides, 5-hydroxy-2-(hydroxymethyl)-4H-pyran-4-on, 4-hydroxyphenyl-☐-D-glucopyranosides and plant extracts. Further substances can be found in the "International Cosmetic Ingredient Dictionary and Handbook" Eleventh Edition 2006, Volume 3, page 2814.

Colorants and Dye Pigment

A list of suitable colorants and pigments can be found in the "International Cosmetic Ingredient Dictionary and Handbook" Eleventh Edition 2006, Volume 3, pages 2670-2677 and "Cosmetology—Theory and Practice" Volume 3, pages 222-223; Editors: K. Schrader, A. Domsch; Verlag für Chemische Industrie, 2005.

Further Fillers

This is understood to include particles and solids which influence light reflection and in this connection increase the proportion of the diffusely reflected light. Thus a soft focus effect is achieved which allows the skin to appear smoother and less wrinkled. Suitable additives are polymethyl silsesquioxanes, bornitride, nylon (Nylon-12), polyethylene (plastic powder), polyethylene/PTFE, dimethicone/vinyl dimethicone crosspolymer (and) lauroyl lysine, dimethicone/vinyl dimethicone crosspolymer (and) alumina, dimethicone/vinyl dimethicone crosspolymer (and) titanium dioxide, dimethicone/vinyl dimethicone crosspolymer, dimethicone/vinyl dimethicone crosspolymer (and) silica, polymethyl methacrylate, silica and silica silylate. These substances are also suitable for the absorption of sebum, which reduces skin shine.

Insect Protecting Agents

Suitable ingredients are inter alia ethyl butylacetylaminopropionate, diethyl toluamide and IR3535 Insect repellent by Merck.

Deodorants and Antiperspirants

Suitable ingredients for the production of antiperspirants with the oil-in-water emulsion compositions of the invention are fragrances, fragrance oils, triclosane, chlorhexidine, sodium hydrogen carbonate, clathrates such as zinc ricinolate and others, ion exchangers, triethylcitrate, o-acyl serine, acyl actylate, aluminium hydroxychloride, sodium aluminium chlorhydroxylactate, aluminium hydroxychloride with propylene glycol and circonium salts such as e.g. z.B. aluminium zirconium tetrachlorohydrex gly and aluminium circonium trichlorohydrex gly. Further antiperspirant active substances are mentioned in "Cosmetology—Theory and Practice" Volume 2, pages 268-269; Editors: K. Schrader, A. Domsch; Verlag für Chemische Industrie, 2005. A special form of antiperspirants are clear gels. These can be produced with the oil-in-water emulsion compositions according to the invention by matching the refraction indexes of the water and oil phases.

Ingredients for Hair Products

The oil-in-water emulsion compositions according to the invention are also suitable for the production of oil-in-water emulsions for hair care. In particular "leave-in" conditioners such as hair conditioners, hair gels, styling gels, hair forming agents, hair bleaching agents and hair colorants are to be mentioned here. The ingredients used in these compositions can be found in "Cosmetology—Theory and Practice" Volume 2; Editors: K. Schrader, A. Domsch; Verlag für Chemische Industrie, 2005.

Additives

Additives as ingredients for cosmetic formulations are defined in: A. Domsch, Die kosmetischen Präparate, Verlag für chem. Industrie, 4. Auflage, 1992; and in: Kosmetikjahrbuch 1995, Verlag für Chemische Industrie, 1995.

The following suitable additives are exemplary but, however, not limiting, as ingredients for the formulations: inorganic and organic acids, bases and buffers, salts, alcohols such as e.g. ethanol, isopropanol, ethylene glycol, polyethylene glycol, propylene glycol, polypropylene glycol, glycol ether and glycerine, thickeners, stabilisers for emulsions such as e.g. xanthan gum, emollients, preservatives, foam stabilisers, defoamers, pearlescents and opacifiers such as e.g. glycol distearate and titanium dioxide, collagen hydrolysate, keratin hydrolysate, silk hydrolysate, anti-dandruff agents such as e.g. zinc pyrithion, salicylic acid, selenium disulfide, sulphur and tar preparations, polymer emulsifiers, vitamins, dyes, UV filters, bentonites, perfume oils, fragrances, styling polymers, moisturizers, plant extracts and further natural and nature-identical raw materials.

The preferred use of the substances according to the invention is the use for the production of cosmetic compositions for the treatment of substances comprising keratin, such as the human skin or human hair. In this connection specific cosmetic formulations according to the invention are creams and lotions for face and body care, creams and lotions for UV radiation protection, self-tanners, skin tighteners and products for the treatment of hyperpigmentation such as age spots and freckles (skin whiteners), make-up removers, pigmented products such as mascaras, eyeliners, lipsticks and liquid make-up (liquid foundation), deodorants and antiperspirants such as e.g. gels, roll-ons, creams and emulsions, "leave-in" conditioners for the hair such as e.g. deep hair conditioners and cures and gels, hair styling products such as e.g. hair gels, styling mousses and creams and hair waxes, hair bleaching agents, hair forming agents, hair waving agents, hair colorants. The substances according to the invention are suitable for use as oil-in-water emulsion and can of course also be used in multiple emulsions.

Various features of the invention are illustrated by the examples presented below.

EXAMPLES

The method of conducting non-whitening test is described below.

The test consisted of measuring the whitening effect of the emulsion applied on a wet substrate. A 3" wide blue painting masking tape (e.g., Scotch-Blue Painter's tape for multi-surfaces #2090 from 3 M™) was taped on a rigid black cardboard. The substrate had an open area of 147 cm$^2$. Water was applied to the blue masking tape with a gloved finger in the amount of 2 mg/cm$^2$. Picture (I) of the wet substrate was taken and used as a control (blank substrate). The camera was set in manual control with an aperture of F 3.1. The lightening and the camera setting conditions were kept constant for picture (I) and picture (II). An emulsion amount of 2 mg/cm$^2$ was applied with a gloved finger. Picture (II) was taken immediately after the application of the emulsion. The digital image file was opened and analyzed in the image analysis software the Image-Pro Plus Software (Media Cybernetics Inc.).

The total intensity of the digital image was obtained by calculating the mean grey pixel value. The total intensity of the picture (I) was obtained by calculating the mean grey pixel value of the blank wet substrate image. The total intensity of picture (II) was obtained by calculating the mean grey pixel value of the treated substrate image. The "whitening" of the treated substrate was compared to the blank substrate (zero whitening) and reported using the following formula:

$$\text{Whitening} = (\text{Intensity}_{Picture(I)} - \text{Intensity}_{Picture(II)}) * (100/\text{Intensity}_{Picture(I)})$$

The whitening is considered significant when it is higher than 20%.

The method of measuring the particle size is described below.

The oil droplet size of the emulsions was measured by light scattering using a Coulter particle size analyzer LS230 (small volume module). For each measurement, the emulsions were pre-diluted to 1:1 with deionized water. The Polarization Intensity Differential Scattering (PIDS) obscuration was around 50% and the run length was 90 seconds.

Table 1 lists the materials used in the experimental section.

TABLE 1

| Chemical Names | Supplier | Commercial name or Abbreviation |
|---|---|---|
| Ammonium acryloyldimethyltaurate/VP copolymer | Clariant | Aristoflex AVC |
| Ammonium acryloyldimethyltaurate/beheneth 25 methacrylate copolymer | Clariant | Aristoflex hmb |
| Acrylates/C10-30 alkylacrylate crosspolymer | Lubrizol | Carbopol 1382 |
| Hydroxypropyl methyl cellulose | Dow | Methocel |
| Polysilicone-25 | Momentive Performance Materials Inc. | Silform EOF |
| PEG 8 dimethicone | Momentive Performance Materials Inc. | Silsoft 840 |
| PEG/PPG 20/23 dimethicone | Momentive Performance Materials Inc. | Silsoft 440 |
| VP/eicosene copolymer | ISP | Ganex V-220 |
| Acrylates/C10-30 alkylacrylate crosspolymer | Lubrizol | Pemulen TR-1 |
| Cyclopentasiloxane and dimethiconol | Momentive Performance Materials Inc. | Silsoft 1215 |
| Polymethylsilsesquiloxane | Momentive Performance Materials Inc. | Silform Flex |

Example 1 was prepared using the method described below.

The different organic sunscreen filters, avobenzone (2.6 grams), homosalate (8.8 grams), octisalate (4.4 grams), octocrylene (8.8 grams) and oxybenzone (5.4 grams), were blended together with a conventional bench-top stirring blade with a mixing speed of 500 RPM. The mixture was heated to 80° C. while mixing until all solids have dissolved. The organic sunscreen filters blend was then cooled down to room temperature. Dicaprylyl carbonate (5 grams) and polysilicone-25 (1 gram) were added to the sunscreen oil blend and mixed until homogeneous.

In a separate beaker, 63.6 grams of deionized water was stirred at high speed to form a strong vortex and 0.13 grams of ammonium acryloyldimethyltaurate/beheneth 25 methacrylate copolymer was added by small increments to the vortex until all the thickener was uniformly dispersed.

The sunscreen/emulsifier blend was added slowly to the aqueous dispersion of ammonium acryloyldimethyltaurate/beheneth 25 methacrylate copolymer while mixing at 300 RPM until it has all been incorporated.

The remaining 0.23 grams ammonium acryloyldimethyltaurate/beheneth 25 methacrylate copolymer was added slowly to the emulsion. The final emulsion was homogenized at 15000 RPM for 5 minutes.

Example 2 was prepared using the method described below.

The different organic sunscreen filters, avobenzone (2.6 grams), homosalate (8.8 grams), octisalate (4.4 grams), octocrylene (8.8 grams) and oxybenzone (5.4 grams), were blended together with a conventional bench-top stirring blade with a mixing speed of 500 RPM. The mixture was heated to 80° C. while mixing until all solids have dissolved. The organic sunscreen filters blend was then cooled to room temperature. Dicaprylyl carbonate (5 grams) and polysilicone-25 (1 gram) were added to the sunscreen oil blend and mixed until homogeneous.

In a separate beaker, 63.6 grams of deionized water was stirred at high speed to form a strong vortex and 0.13 grams of ammonium acryloyldimethyltaurate/VP copolymer was added by small increments to the vortex until all the thickener was uniformly dispersed.

The sunscreen/emulsifier blend was added slowly to the aqueous dispersion of ammonium acryloyldimethyltaurate/VP copolymer while mixing at 300 RPM until it has all been incorporated.

The remaining 0.23 grams ammonium acryloyldimethyltaurate/VP copolymer was added slowly to the emulsion. The final emulsion was homogenized at 15000 RPM for 5 minutes.

Example 3 was prepared using the method described below.

The organic sunscreen filters, avobenzone (2.6 grams), homosalate (8.8 grams), octisalate (4.4 grams), octocrylene (8.8 grams) and oxybenzone (5.4 grams), were blended together with a conventional bench-top stirring blade with a mixing speed of 500 RPM. The mixture was heated to 80° C. while mixing until all solids have dissolved. The organic sunscreen filters blend was then cooled down to room temperature.

In a separate beaker, a neutralized gel of 1% carbopol 1382 was prepared. 20 grams of the 1% carbopol 1382 was blended with 47 grams of water and 3 g of Peg-8 dimethicone. The oil phase was incorporated by small increment in the water phase using an overhead homogenizer.

Comparative Example 1 was prepared in the similar manner as Example 3 with the ingredient and amount indicated in Table 2. The composition of Comparative Example 1 has an average particle size lower than 5 microns.

The components and the amounts of each component for Examples 1-3 and Comparative Example 1 are presented in Table 2.

TABLE 2

| | Example 1 | Example 2 | Example 3 | Comparative Example 1 |
|---|---|---|---|---|
| Ammonium acryloyldimethyltaurate/VP copolymer | | 0.36 | | |
| Ammonium acryloyldimethyltaurate/beheneth 25 methacrylate copolymer | 0.36 | | | |
| Acrylates/C10-30 alkylacrylate crosspolymer | | | 0.2 | 0.3 |
| Hydroxypropyl methyl cellulose | | | | 0.3 |
| Avobenzone | 2.6 | 2.6 | 2.6 | 2.6 |
| Homosalate | 8.8 | 8.8 | 8.8 | 8.8 |
| Octisalate | 4.4 | 4.4 | 4.4 | 4.4 |
| Octocrylene | 8.8 | 8.8 | 8.8 | 8.8 |
| Oxybenzone | 5.4 | 5.4 | 5.4 | 5.4 |
| Dicaprylyl carbonate | 5 | 5 | | |
| Polysilicone-25 | 1 | 1 | | |
| PEG 8 dimethicone | | | 3 | |
| PEG/PPG 20/23 dimethicone | | | | 0.3 |
| sorbitan oleate | | | | 0.5 |
| VP/eicosene copolymer | | | | 1 |
| Pemulen TR-1 (Acrylates/C10-30 alkylacrylate crosspolymer) | | | | 0.3 |
| glycerin | | | | 4 |
| Water | Sufficient quantity to 100 | Sufficient quantity to 100 | Sufficient quantity to 100 | Sufficient quantity to 100 |

Example 4, a polishing emulsion, was prepared using the method described below.

The oil phase was prepared by blending 30 grams of mineral oil and 1 gram of polysilicone-25. In a separate beaker, 68.6 grams of deionized water was stirred at high speed to form a strong vortex and 0.13 grams of ammonium acryloyldimethyltaurate/VP copolymer was added by small increments to the vortex until all the thickener was uniformly dispersed.

The oil phase was added slowly to the aqueous dispersion of ammonium acryloyldimethyltaurate/VP copolymer while mixing at 300 RPM until it had all been incorporated.

The remaining of 0.23 grams ammonium acryloyldimethyltaurate/VP copolymer was added slowly to the emulsion. The final emulsion was homogenized at 15000 RPM for 5 minutes.

The components and the amounts of each component for Example 4 are presented in Table 3.

TABLE 3

| Ingredients | Wt % |
|---|---|
| Ammonium acryloyldimethyltaurate/VP copolymer | 0.36 |
| Mineral oil | 30 |
| Polysilicone-25 | 1 |
| water | Sufficient quantity to 100 |

Example 5, a hair shine emulsion, was prepared using the method described below.

The oil phase was prepared by blending 18 grams of cyclomethicone, 7.5 grams of silsoft 1215, 4.5 grams of silform flex and 1 gram of polysilicone-25. In a separate beaker, 68.6 grams of deionized water was stirred at high speed to form a strong vortex and 0.13 grams of ammonium acryloyldimethyltaurate/VP copolymer was added by small increments to the vortex until all the thickener was uniformly dispersed.

The oil phase was added slowly to the aqueous dispersion of ammonium acryloyldimethyltaurate/VP copolymer while mixing at 300 RPM until it had all been incorporated.

The remaining 0.23 grams of ammonium acryloyldimethyltaurate/VP copolymer as added slowly to the emulsion. The final emulsion was homogenized at 15000 RPM for 5 minutes.

The components and the amounts of each component for Example 5 are presented in Table 4.

TABLE 4

| Ingredients | Wt % |
|---|---|
| Ammonium acryloyldimethyliaurate/VP copolymer | 0.36 |
| Silsoft 1215 | 7.5 |
| Silform Flex | 4.5 |
| cyclodimethicone | 18 |
| Polysilicone-25 | 1 |
| water | Sufficient quantity to 100 |

The particle size and whitening effects of Examples 1-5 are measured and compared with Comparative Examples 1-3, in which Comparative Example 1 is described in Table 2, Comparative Example 2 is a commercial sun protection lotion SPF 100 from Neutrogena. Comparative Example 3 is a commercial sun protection lotion SPF 30 from Coppertone.

Table 5 shows the particle size and whitening measurements from the emulsion Examples 1-5 and Comparative Examples 1-3.

TABLE 5

Particle size and whitening measurements

| Samples | Average particle size (micron) | Whitening On wet substrate (%) | Emulsion stability 4 weeks storage at 50° C. |
|---|---|---|---|
| Example 1 | 13 | 14 | yes |
| Example 2 | 23 | 1 | yes |
| Example 3 | 25 | 3 | yes |
| Example 4 | 21 | −5 | yes |
| Example 5 | 35 | 3 | yes |
| Comparative Example 1 | 4 | 42 | yes |
| Comparative Example 2 | 0.7 | 44 | yes |
| Comparative Example 3 | 3 | 31 | yes |

As can be seen from Table 5, the emulsions with average particle size higher than 5 microns did not produce significant whitening (<20%) when applied on the wet substrate. In contrast, Comparative Examples had an average particle size lower than 5 microns and had significant whitening (>20%) when applied on the wet substrate.

Example 1 and Example 2 were also tested for their water-resistant sun protection property. The method of measuring the SPF is described below.

The substrate used for SPF measurements were "vitro skin" from IMS Inc. (Portland, Me.) hydrated at room temperature overnight in an hermetic plastic chamber containing 200 gm of a 30 wt % solution of glycerin in water (substrates do not touch the solution). The SPF measurements were obtained using the transmittance analyzer, Labsphere UV1000. Labsphere UV1000 is designed to accurately measure SPF in the range of 30 or below. For SPF value above 40, the measurements should to be confirmed in vivo by clinical trials.

With a syringe, 0.06 g of oil-in-water emulsion composition of Example 1 or Example 2 was weighed on a piece of hydrated vitro skin. With a gloved finger, the emulsion was evenly spread and rubbed over the surface of the vitro skin for 30 seconds. Vitro skin sample was air dried for 20 minutes. To obtain dry SPF values, a measurement of transmittance of the hydrated vitro skin was performed, then vitro-skin treated with oil-in-water emulsion composition of Example 1 or Example 2 was measured at 5 different spots (the center and four corners). After the measurements of the dry SPF, the treated vitro-skin was immersed in the water bath for consecutive 20 minutes. After the immersion in the water, the treated vitro skin was air dried for 20 minutes. The SPF values of the treated vitro-skin after immersion were measured at 5 different spots. Table 6 lists the SPF values before and after water immersion.

TABLE 6

|  | Example 1 | Example 2 |
| --- | --- | --- |
| In-vitro dry SPF | 41 | 42 |
| SPF after 40 min water immersion | 43 | 49 |

As shown in Table 6, Examples 1 and 2 both possess desired properties of a high SPF (SPF>30) and a high water resistance.

These examples are to be construed as exemplary in nature only and are not intended in any way to limit the appended claims. It is contemplated that a person having ordinary skill in the art would be able to produce obvious variations of the subject matter and disclosures herein contained that would be by reason of such ordinary skill within the literal or equitable scope of the appended claims.

What is claimed is:

1. An oil-in-water emulsion-forming composition comprising:
(i) polysiloxane possessing at least one hydrophilic moiety having the general formula (II)

[M$_a$D$_b$T$_c$Q$_d$]$_e$ (II)

wherein
M=R$^4$R$^5$R$^6$SiO$_{1/2}$,
D=R$^7$R$^8$SiO$_{2/2}$,
T=R$^9$SiO$_{3/2}$,
Q=SiO$_{4/2}$,
with
a=1-10
b=0-1000
c=0-1
d=0-1
e=1-10
wherein
R$^4$, R$^5$, R$^6$, R$^7$, R$^8$ and R$^9$ are each independently an organic group, which comprises at least one group R$^{10}$, which is selected from:
R$^{11}$=—Z-(A-E)$_y$, wherein
Z=a bivalent or trivalent straight-chained, cyclic or branched, saturated or unsaturated C$_2$ to C$_{20}$-hydrocarbon group, which can comprise one or more groups selected from —O—, —NH—,

and can be substituted by one or more OH groups,
A is a bivalent group which is selected from the group which comprises:

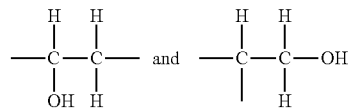

y=1 or 2
E is selected from the group which comprises:
E$^2$=—O—C(O)—R$^{12}$,
wherein R$^{12}$ is a straight-chained, cyclic or branched, saturated or unsaturated hydrocarbon group with up to 50 carbon atoms, which can comprise one or more groups selected from —O—, —NH—, —NR$^{13}$—, —C(O)— and is substituted by one or more OH groups, wherein R$^{13}$ is a straight-chained, cyclic or branched, saturated or unsaturated hydrocarbon group with up to 6 carbon atoms, and E$^3$=

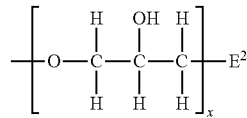

wherein E$^2$ is as defined above, and x =1-4,
E$^4$=—NR$^{14}$R$^{15}$, wherein
R$^{14}$ and R$^{15}$ are the same or different and are selected from the group which comprises: hydrogen and straight-chained, cyclic or branched, saturated or unsaturated hydrocarbon group with up to 30 carbon atoms, which can comprise one or more groups selected from —O—, —NH—, —NR$^{13}$—
wherein R$^{13}$ is as defined above, —C(O)—, and can be substituted by one or more OH— and/or H$_2$N— groups,
R$^{16}$=—Z-E$^2$ wherein E$^2$ is as defined above, and
R$^{17}$=—Z-E$^5$, wherein E$^5$=—NH—C(O)—R$^{14}$, wherein R$^{14}$ is a defined above,
R$^{10}$ in addition to at least one of R$^{11}$, R$^{16}$ and R$^{17}$ may be R$^{18}$=—Z-E$^1$, wherein E$^1$ is —O—C(O)—R$^{19}$,
wherein R$^{19}$ is a straight-chained, cyclic or branched, saturated or unsaturated hydrocarbon group with up to 50 carbon atoms, which can comprise one or more groups selected from —O—, —NH—, —NR$^{13}$—, —C(O)—, wherein R$^{13}$ is as defined above, but has no hydroxyl substituent;
(ii) polymeric aqueous thickener; and,
(iii) oil,
the oil-in-water emulsion-forming composition forming a oil-in-water emulsion upon addition of an emulsion-forming amount water (iv) thereto, the average particle size of oil (iii) in the emulsion being at least 5 microns, the emulsion when applied to a water-wet substrate exhibiting no significant whitening effect.

2. The oil-in-water emulsion-forming composition of claim 1 wherein the hydrophilic moiety of polysiloxane (i) is selected from the group consisting of polyether group, sugar group, polyhydroxylated hydrocarbon group, and ionic group.

3. The oil-in-water emulsion-forming composition of claim 1 wherein polymeric aqueous thickener (ii) is selected from the group consisting of crosslinked polyacrylate polymer, polyacrylamide, copolymer, anionic or cationic crosspolymer which can produce a yield point in water.

4. The oil-in-water emulsion-forming composition of claim 1 wherein polymeric aqueous thickener (ii) is selected from the group consisting of carbopol, ammonium acryloyldimethyltaurate/VP copolymer, ammonium acryloyldimethyltaurate/beheneth-25 methacrylate crosspolymer, carboxyvinyl polymer, acrylate/C10-C30-alkylacrylate copolymer, polyacrylamide/C13-14 isoparaffin/Laureth 7, acrylamide/sodium acryloyldimethyltaurate copolymer/isohexadecane/polysorbate 80, 2-acrylamido-2-methylpropanesulfonic acid polymer and copolymer, hydroxyethylcellulose, polysaccharide, gum, and mixtures thereof.

5. The oil-in-water emulsion-forming composition of Claim 1 wherein the average particle size of oil (iii) in the emulsion is at least 10 microns.

6. The oil-in-water emulsion-forming composition of claim 1 wherein oil (iii) is selected from the group consisting of triglyceride, silicone, hydrocarbon, hydrophobic polymer, fatty alcohol, natural wax and fat, fatty acid ester of monoalcohol, and mixtures thereof.

7. The oil-in-water emulsion-forming composition of claim 1 wherein the whitening effect of the oil-in-water emulsion composition formed therefrom when applied to a water-wet substrate is not greater than 20%.

8. A skin care product, hair care product, polishing product, gloss enhancement product or water resistance treatment product formulated with the oil-in-water emulsion-forming composition of claim 1.

9. The oil-in-water emulsion-forming composition of claim 1 wherein the water-wet substrate is selected from the group consisting of skin, hair, textile, leather, wood, stone, tile, rubber, metal surface, glass, and plastic surface.

10. The oil-in-water emulsion composition obtained from the addition of an emulsion-forming amount of water (iv) to the oil-in-water emulsion-forming composition of claim 1.

11. The oil-in-water emulsion composition of claim 10 wherein polysiloxane (i) is employed in the amount of from 0.05% to 10% by weight based on the total weight of the oil-in-water emulsion composition.

12. The oil-in-water emulsion composition of claim 10 wherein polymeric aqueous thickener (ii) is employed in the amount of from 0.05% to 10% by weight based on the total weight of the oil-in-water emulsion composition.

13. The oil-in-water emulsion composition of claim 10 wherein oil (iii) is employed in the amount of from 20% to 60% by weight based on the total weight of the oil-in-water emulsion composition.

14. The oil-in-water emulsion composition of claim 10 wherein oil (iii) and/or water (iv) contains at least one optional component.

15. The oil-in-water emulsion composition of claim 10 formulated as a skin care product, hair care product, polishing product, gloss enhancement product or water resistance treatment product.

16. An oil-in-water emulsion composition comprising:
(i) a polysiloxane having the general formula (II)

$$[M_a D_b T_c Q_d]_e \qquad (II)$$

wherein
$M = R^4 R^5 R^6 SiO_{1/2}$,
$D = R^7 R^8 SiO_{2/2}$,
$T = R^9 SiO_{3/2}$,
$Q = SiO_{4/2}$,
with
a=1-10
b=0-1000
c=0-1
d=0-1
e=1-10
wherein
$R^4$, $R^5$, $R^6$, $R^7$, $R^8$ and $R^9$ are each independently an organic group, which comprises at least one group $R^{10}$, which is selected from:
$R^{11}$=—Z-(A-E)$_y$, wherein
Z=a bivalent or trivalent straight-chained, cyclic or branched, saturated or unsaturated $C_2$ to $C_{20}$-hydrocarbon group, which can comprise one or more groups selected from —O—, —NH—,

and can be substituted by one or more OH groups,
A is a bivalent group which is selected from the group which comprises:

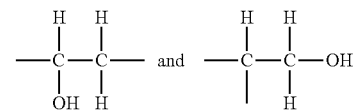

y=1 or 2
E is selected from the group which comprises:
$E^2$=—O—C(O)—$R^{12}$,
wherein $R^{12}$ is a straight-chained, cyclic or branched, saturated or unsaturated hydrocarbon group with up to 50 carbon atoms, which can comprise one or more groups selected from —O—, —NH—, —NR$^{13}$—, —C(O)— and is substituted by one or more OH groups, wherein $R^{13}$ is a straight-chained, cyclic or branched, saturated or unsaturated hydrocarbon group with up to 6 carbon atoms, and
$E^3$=

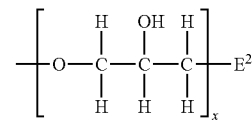

wherein $E^2$ is as defined above, and x=1-4,
$E^4$=—NR$^{14}$R$^{15}$, wherein
$R^{14}$ and $R^{15}$ are the same or different and are selected from the group which comprises: hydrogen and straight-chained, cyclic or branched, saturated or unsaturated hydrocarbon group with up to 30 carbon atoms, which can comprise one or more groups selected from —O—, —NH—, —NR$^{13}$—, wherein $R^{13}$ is as defined above, —C(O)—, and can be substituted by one or more OH— and/or $H_2N$— groups, $R^{16}$=—Z-$E^2$ wherein $E^2$ is as defined above, and $R^{17}$=—Z-$E^5$, wherein $E^5$=—NH—C(O)—$R^{14}$, wherein $R^{14}$ is a defined above, $R^{10}$ in addition to at least one of $R^{11}$, $R^{16}$ and $R^{17}$ may be $R^{18}$=—Z-$E^1$, wherein $E^1$ is —O—C(O)—$R^{19}$, wherein $R^{19}$ is a straight-chained, cyclic or branched, saturated or unsaturated hydrocarbon group with up to 50 carbon atoms, which can comprise one or more groups selected from —O—, —NH—, —$NR^{13}$—, —C(O)—, wherein $R^{13}$ is as defined above, but has no hydroxyl substituent;

(ii) a polymeric aqueous thickener selected from the group consisting of crosslinked polyacrylate polymer, polyacrylamide, copolymer, anionic or cationic crosspolymer which can produce a yield point in water;

(iii) an oil selected from the group consisting of triglyceride, silicone, hydrocarbon, hydrophobic polymer, fatty alcohol, natural wax and fat, fatty acid ester of monoalcohol, and mixtures thereof; and, (iv) an emulsion-forming amount of water, the average particle size of oil (iii) in the emulsion being at least 5 microns, the emulsion when applied to a water-wet substrate exhibiting no significant whitening effect.

17. The oil-in-water emulsion composition of claim 16 wherein the average particle size of oil (iii) in the emulsion is at least 10 microns.

18. The oil-in-water emulsion composition of claim 16 wherein the whitening effect of the emulsion when applied to a water-wet substrate is not greater than 20%.

19. The oil-in-water emulsion composition of claim 16 wherein oil (iii) and/or water (iv) contains at least one optional component.

20. The oil-in-water emulsion composition of claim 16 formulated as a skin care product, hair care product, polishing product, gloss enhancement product or waterresistance treatment product.

* * * * *